US011639294B2

(12) United States Patent
Favaro et al.

(10) Patent No.: US 11,639,294 B2
(45) Date of Patent: May 2, 2023

(54) METHOD FOR PRODUCING A NANOSTRUCTURED COMPLEX (CFI-1), A PROTEIN-ASSOCIATED NANOSTRUCTURED COMPLEX (MRB-CFI-1) AND USE

(71) Applicant: UNIVERSIDADE ESTADUAL DE CAMPINAS—UNICAMP, Campinas (BR)

(72) Inventors: Wagner José Favaro, Campinas (BR); Nelson Eduardo Duran Caballero, Paulinia (BR)

(73) Assignee: UNIVERSIDADE ESTADUAL DE CAMPINAS—UNICAMP

( * ) Notice: Subject to any disclaimer, the term of this patent is extended or adjusted under 35 U.S.C. 154(b) by 234 days.

(21) Appl. No.: 17/236,861

(22) Filed: Apr. 21, 2021

(65) Prior Publication Data
US 2021/0238046 A1    Aug. 5, 2021

Related U.S. Application Data

(62) Division of application No. 16/617,493, filed as application No. PCT/BR2018/000031 on Jun. 14, 2018, now Pat. No. 11,136,242.

(30) Foreign Application Priority Data

Jun. 14, 2017   (BR) .................. 10 2017 012768 0

(51) Int. Cl.
| | |
|---|---|
| *C01C 1/02* | (2006.01) |
| *A61P 31/00* | (2006.01) |
| *A61P 35/00* | (2006.01) |
| *A61K 39/39* | (2006.01) |
| *C01B 25/02* | (2006.01) |
| *C01F 5/32* | (2006.01) |
| *A61K 38/00* | (2006.01) |
| *B82Y 5/00* | (2011.01) |
| *B82Y 40/00* | (2011.01) |

(52) U.S. Cl.
CPC ............. *C01C 1/026* (2013.01); *A61K 39/39* (2013.01); *A61P 31/00* (2018.01); *A61P 35/00* (2018.01); *C01B 25/02* (2013.01); *C01F 5/32* (2013.01); *A61K 38/00* (2013.01); *B82Y 5/00* (2013.01); *B82Y 40/00* (2013.01)

(58) Field of Classification Search
CPC ................................ A61P 35/00; A61K 33/06
See application file for complete search history.

(56) References Cited

U.S. PATENT DOCUMENTS

| | | | |
|---|---|---|---|
| 5,073,630 A | 12/1991 | Nunes et al. ............ 530/400 |
| 5,900,410 A | 5/1999 | Hartmann ................ 514/81 |
| 6,476,082 B1 | 11/2002 | Green ..................... 516/88 |
| 8,889,153 B2 | 11/2014 | Nunes ................. A61K 45/06 |
| 9,295,682 B2 | 3/2016 | Nunes ................. A61K 31/661 |
| 2012/0251441 A1 | 10/2012 | Nunes ..................... 424/1.49 |
| 2014/0341940 A1 | 11/2014 | Nunes ................. A61K 9/0014 |
| 2016/0166683 A1 | 6/2016 | Nunes ................. A61K 39/39 |

FOREIGN PATENT DOCUMENTS

| | | | |
|---|---|---|---|
| BR | PI0704797 | 3/2009 | ......... A61K 31/4045 |
| WO | WO2009097670 | 8/2009 | ............ A61K 45/00 |
| WO | WO2013067608 | 5/2013 | ............ A61P 31/12 |

OTHER PUBLICATIONS

U.S. Appl. No. 16/617,493, filed Nov. 26, 2019
U.S. Appl. No. 17/236,839, filed Apr. 21, 2021, Favaro et al.
U.S. Appl. No. 17/236,848, filed Apr. 21, 2021, Favaro et al.
Afsharimoghaddam et al., Controversial roles played by toll like receptor 4 in urinary bladder cancer; A systematic review, Life Sciences 158 (2016) 31-36, abstract only (2 pgs).
Allen et al., Multilocular Prostatic Cystadenoma with High-Grade Prostatic Intraepithelial Neoplasia, Case Report, Elsevier Science Inc. 2003 (3 pgs).
American Cancer Society. *Cancer Facts & Figures 2016*, Atlanta: American Cancer Society; 2016 (72 pgs).
Askeland et al., Bladder Cancer Immunotherapy: BCG and Beyond, Advances in Urology, vol. 2012, Article ID 181987 (13 pgs).
Battistoni et al., Phosphate Removal in Anaerobic Liquors by Struvite Crystallization Without Addition of Chemicals: Preliminary Results, Wat. Res. vol. 31, No. 11, 1997 (5 pgs).
Ben Omar et al., Struvite Crystallization on *Myxococcus* Cells, Chemopshere, vol. 36, No. 3, 1998 (7 pgs).
Diaz et al., Potential therapeutic strategies for non-muscle invasive bladder cancer based on association of intravesical immunotherapy with P-maPa and systemic administration of cisplatin and doxorubicin, IBJU | Immunotherapy and Chemotherapy on Bladder Cancer, vol. 42 (5): 942-954, Sep.-Oct., 2016 (13 pgs).
Epstein et al., The World Health Organization/International Society of Urological Pathology Consensus Classification of Urothelial (Transitional Cell) Neoplasms of the Urinary Bladder, The American Journal of Surgical Pathology, vol. 22(12), Dec. 1998 (41 pgs).
Favaro et al., Effects of P-MAPA Immunomodulator on Toll-Like Receptors and p53: Potential Therapeutic Strategies for Infectious Diseases and Cancer, Infectious Agents and Cancer 2012, 7:14 (15 pgs).
Garcia et al., Alterations in ubiquitin ligase Siah-2 and its corepressor N-CoR after P-MAPA immunotherapy and anti-androgen therapy: new therapeutic opportunities for non-muscle invasive bladder cancer, Int J Clin Exp Pathol 2015; 8(5):4427-4443 (17 pgs).

(Continued)

*Primary Examiner* — Andrew S Rosenthal
(74) *Attorney, Agent, or Firm* — Hayes Soloway P.C.

(57) ABSTRACT

Disclosed is a method for treating cancer in a subject by administering to the subject a compound selected from $NH_4MgPO_4 \times 6H_2O$, $(NH_4)2MgH_2(PO_4)_2 \times 4H_2O$, $(NH_4)2Mg_3(HPO_4)_4 \times 8H_2O$ and $NH_4MgPO_4 \times H_2O$ associated or not to hydrolytic enzymes, which are known to have immunomodulatory activities.

3 Claims, 20 Drawing Sheets

(56) References Cited

OTHER PUBLICATIONS

Gomes da Silva, J.A., Estimativa 2016, Incidencia de Cancer no Brazil (no translation available), Ministerio da Saude, Instituto Nacional de Cancer (INCA) 2015 (126 pgs).

Guo et al., Multi-Class Carcinogenic DNA Adduct Quantification in Formalin-Fixed Paraffin-Embedded Tissues by Ultra-Performance Liquid Chromatograpy-Tandem Mass Spectrometry, Anal Chem. May 3, 2016; 88(9) (17 pgs).

Hillner et al., Impact of $^{18}$F-FDG PET Used After Initial Treatment of Cancer: Comparison of the National Oncologic PET Registry 2006 and 2009 Cohorts, Society of Nuclear Medicine, Inc., 2012 (8 pgs).

International Preliminary Report on Patentability issued in application No. PCT/BR2018/000031, dated Dec. 17, 2019 (18 pgs).

International Search Report and Written Opinion issued in application No. PCT/BR2018/000031, dated Aug. 15, 2018 (23 pgs).

Ishizaki, T. et al. Electrochimica Acta 62 (2012) 19-29 (Year: 2012).

Jimenez-Lopez et al., Biomineralization induced by Myxobacteria, Communicating Current Research and Educational Topics and Trends in Applied Microbiology, A. Mendez-Vilas (Ed.), Formatex 2007 (12 pgs).

Kotina, A.N. et al. "Controlled Precipitation of Sparingly Soluble Phosphate Salts Using Enzymes. II. Precipitation of Struvite" Crystal Growth & Design, vol. 9, No. 11, 2009, pp. 4642-4652 (Year: 2009).

Martins Neto, A.A., Desvio da reposta imunológica deflagrada por morte cellular em melanoma esperimental pelo imunoestimulador P-MAPA: uma potential estratégia antitumoral dependente da ativação de receptores TOLL-LIKE? (no translation available) Tese (Doutorado em Ciencias)—Faculadade de Medicina, Universidade de São Paulo. São Paulo, p. 100, 2017 (100 pgs).

Nezos et al., Detection of circulating tumor cells in bladder cancer patients, Cancer Treatment Reviews 35, 2009 (8 pgs).

Notice of Allowance issued in U.S. Appl. No. 16/617,493, dated May 19, 2021, 26 pages.

Office Action issued in U.S. Appl. No. 16/617,493, dated Feb. 22, 2021, 9 pages.

Okorokov et al., Free and Bound Magnesium in Fungi and Yeasts, Folia Microbiol. 20 (1975) (7 pgs).

Poon et al., Mutation signatures implicate aristolochic acid in bladder cancer development, Genome Medicine, 2015 (10 pgs).

Ramlogan, M.V. et al., "An investigation of the thermal behavior of magnesium ammonium phosphate hexahydrate" J Therm Anal Calorim (2016) 123:145-152 (Year: 2016).

Rivadeneira et al., Influence of Ammonium Ions on Calcite and Struvite Formation by *Azotobacter* in Chemically Defined Media, Folia Microbiol. 30, 1985 (3 pgs).

Stefov, V. et al. "Infrared and Raman spectra of magnesium ammonium phosphate hexahydrate (struvite) and its isomorphous analogues. III. Spectra of protiated and partially deuterated magnesium ammonium phosphate. hexahydrate" Journal of Molecular Structure 752 (2005) 60-67 (Year: 2005).

Smirnov et al., Formation of insoluble magnesium phosphates during growth of the archaea *Halorubrum distributum* and *Halobactrium salinarium* and the bacterium *Brevibacterium antiquum*, FEMS Microbiology. Ecology 52, 2005 (9 pgs).

TNM Classification of Malignant Tumours, edited by Sobin et al., Wiley-Blackwell, Seventh Edition, 2009 (332 pgs).

Zeegers et al., The Impact of Characteristics of Cigarette Smoking on Urinary Tract Cancer Risk, A Meta-Analysis of Epidemiologic Studies, American Cancer Society, 2000 (10 pgs).

METHOD FOR PRODUCING A NANOSTRUCTURED COMPLEX (CFI-1), A PROTEIN-ASSOCIATED NANOSTRUCTURED COMPLEX (MRB-CFI-1) AND USE

CROSS REFERENCE TO RELATED APPLICATION

This application is a divisional application of U.S. patent application Ser. No. 16/617,493, filed Nov. 26, 2019, the contents of which are incorporated herein by reference.

FIELD OF THE INVENTION

The present invention refers to a process of obtaining an inorganic nanostructured complex (CFI-1), a protein-associated nanostructured complex (MRB-CFI-1) and use.

The main technology application is the treatment of urinary bladder cancer, both in animals and in humans. Its antitumor activity is unique and a potentially substitute for other commercial antineoplastic drugs.

BACKGROUND OF THE INVENTION

All organs of the urogenital tract are potential spots for malignant tumors. The incidence and type vary from organ to organ. Urinary bladder cancer (CB) represents the second most common malignant disease of the urinary tract (Siegel et al., 2012; American Cancer Society, 2016).

The American Cancer Society estimated about 76,960 new cases of CB in 2016 in the United States, being 58,950 in men and 18,010 in women. The estimate also predicted 16,390 deaths due to CB, being 11,820 in men and 4,570 in women (American Cancer Society, 2016). According to data from the National Cancer Institute (INCA, 2016), the estimate for Brazil in 2016 was 9,670 new cases of CB, being 7,200 in men and 2,470 in women. In 2013, 3,642 deaths were reported due to CB, being 2,542 in men and 1,099 in women, thus demonstrating a drastic increase in the prevalence of this type of tumor.

More than 70% of the incidence of CB is superficial (pTis, pTa and pT1), of non-invasive tumor (CBNMI), and the occurrence of an invasive disease is occasional (Askeland et al., 2012). However, 50% of invasive non-muscle tumors recurrence to 4 years after treatment and 11% evolve to the invasive phenotype (Askeland et al., 2012).

The histological staging of CB is determined by the depth of tumor invasion of the bladder wall and will depend on the transurethral resection (RTU) of the tumor, by endoscopic approach, for a correct diagnosis. Fragments of superficial and deep resection should be analyzed separately (Epstein et al., 1998; Epstein, 2003). The Tumour Node Metasiasis (TNM) classification 2009 (UICC—Union for Cancer Control) is used for staging.

A significant number of risk factors have been related to the development of CB. According to record data from the INCA population database, the greatest risk factor for the development of CB is smoking, accounting for about 66% of new cases in men and 30% in women (INCA, 2016). In the meta-analysis of epidemiological studies of Zeegers et al. (2000) on the impact of smoking characteristics on the risk of urinary tract cancer, smoking was appointed as a factor that substantially increases the risk for the development of bladder cancer. Cigarettes have dozens of toxic substances, including aromatic amines and N-nitrous analogues of MNU (N-methyl-N-nitrosourea), a potent carcinogen.

Another potential risk factor for the development of CB is occupational exposure to aromatic amines by workers from rubber, textile and ink industries, and infection by *Schistosoma haematobiun*, that is endemic in Mediterranean countries, such as Egypt (Zeegers et al., 2000; Poon et al., 2015; Rosenquist & Grollman, 2016). Exposure to certain substances such as arsenic, which may be present in water supplies, aristolochic acid present in many medicinal plants and pioglitazone present in drugs for the treatment of diabetes are associated as a risk factor (Poon et al., 2015; Rosenquist & Grollman, 2016).

According to the American Cancer Society, the reduced intake of liquids can be a risk factor, since an individual who ingests high amounts of liquids, mainly water, tends to eliminate chemicals more quickly, taking into consideration that this will tend to deflate the bladder more frequently (American Cancer Society, 2016).

In general, CB is about 3 to 4 times more common in men than in women (Nezos et al., 2009). On the other hand, women survival is worse with this type of tumor. It is speculated that the high aggressiveness of bladder cancer in women is due to hormonal imbalance, which arises from the fifth decade of life. Although the urinary bladder is secondarily regulated by steroid sex hormones, the normal urothelial and tumor urothelial are responsive to androgens and estrogens (Garcia et al., 2015). Garcia et al. (2015) demonstrated for the first time in rats chemically induced to CBNMI that increased protein levels of ubiquitin ligase SIAH-2 upregulated the androgenic receptors and decreased levels of estrogen receptors, culminating in the escape of neoplastic urothelial cells from the immune system. These same authors found that the levels of immune system receptors, toll-like receptors (TLRs) were decreased in CBNMI and associated this effect with the increase of SIAH-2 levels and androgenic receptors.

The primary treatment of non-muscle invasive bladder cancer (NMIBC) is based on surgical treatment through transurethral resection (RTU), followed by intravesical immunotherapy with *Bacillus* Calmette-Guerin (BCG), for decreasing recurrence and preventing tumor progression. However, the use of living and attenuated organisms can cause side effects and difficulty in predicting the immune and antitumor response. The use of BCG is limited in NMIBC-due to treatment failure, adverse effects and intolerance occurring in more than two-thirds of patients. Although the use of RTU with chemotherapy or adjuvant immunotherapy represents an important breakthrough in the treatment of CBNMI, the management of this tumor, especially for high-grade tumors, remains a challenge due to the high recurrence rates and progression to invasive and/or metastatic muscle phenotypes. The surgical option for such cases, partial or total cystectomy, is often associated with high rates of morbidity and mortality. Furthermore, for some patients, cystectomy is not an available option due to the presence of concomitant comorbidities. Thus, the development of new therapeutic modalities that prevent disease progression, allow the preservation of the organ and the quality of life of patients and, finally, provide an option for those who are ineligible for cystectomy, is of utmost importance. Compounds that are able to act as agonists of the receptors of the immune system (toll-like receptors) can represent promising candidates to be developed as medicines against cancer.

In this context, the use of the biological response modifier—inorganic phosphate complex 1 (MRB-CFI-1) stands out, which has been proposed with promising results in the treatment of NMIBC. Moreover, the invention of this new nanodrug for the treatment of CBNMI presents great efficiency, low toxicity and is economically viable, with great reproducibility and yield. After experiments with laboratory animals and clinical-veterinary protocol in dogs with CBNMI, the invention presents great potential for use in humans.

BRIEF DESCRIPTION OF THE INVENTION

The present invention refers to a process of obtaining an inorganic nanostructured complex (CFI-1), a protein-associated nanostructured complex (MRB-CFI-1) and use.

The nanostructured complex (CFI-1) comprises inorganic phosphate, with a size ranging from 190.0 to 310.3±36.4 nm, polydispersity of 0.563 and zeta potential of −22.6±4.15 mV.

The protein-associated nanostructured complex (MRB-CFI-1) comprises protein-associated phosphates, with a size ranging from 318.0 to 477.1±146 nm, polydispersity of 0.9 and zeta potential of −28.60±6.74 mV.

Further objects are the use of the complexes obtained (CFI-1) and (MRB-CFI-1) to treat cancer, preferably of prostate, bladder, colorectal, mastocytoma and lymphoma.

Although the compounds $NH_4MgPO_4 \times 6H_2O$, $(NH_4)_2MgH_2(PO_4)_2 \times 4H_2O$, $(NH_4)_2Mg_3(HPO_4)_4 \times 8H_2O$ and $NH_4MgPO_4 \times H_2O$ are described in the literature, associated or not with hydrolytic proteins, they are objects to treat cancer in this invention. The present invention also discloses the mechanisms of the aforementioned complexes in activating the immune system, both epithelial (local) and systemic against tumors.

BRIEF DESCRIPTION OF THE FIGURES

In order to achieve a full and complete view of the object of this invention, referenced figures are presented below, as follows.

invading the connective mucosa and focal squamous differentiation, (e) Flat carcinoma in situ (pTis), characterized by cell atypia: bulky nuclei with reduced cytoplasm and prominent nucleoli (arrows), (g), (h) flat hyperplasia composed of several cell layers in the urothelium, but with no cytological atypia. a-h: Lp—connective mucosa, M—own muscular layer, Ur—urothelium.

Figure 15:
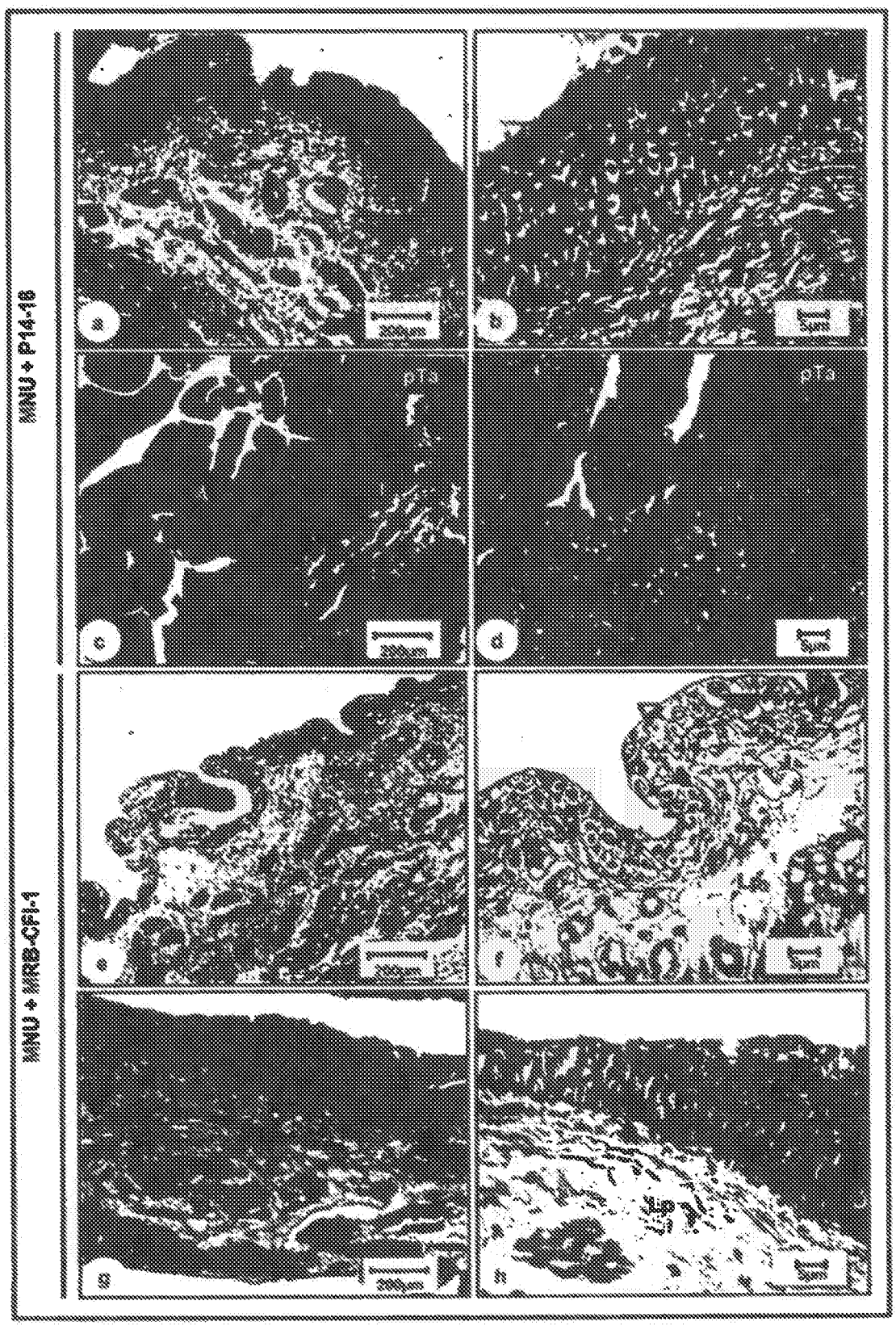

FIG. 15: Photomicrographs of the urinary bladders from groups MNU+P14-16 (a, b, c, d) and MNU+MRB-CFI1 (e, f, g, h). (a), (b), (g), (h) Flat hyperplasia consisting of several cell layers in the urothelium: basal cell layer, middle cell layer and superficial layer, but without cytological atypia. (c), (d) noninvasive urothelial carcinoma (pTa) characterized by papillary lesions and urothelial cells with disordered arrangement and with loss of polarity; mitotic figures (arrows), (e), (f) Normal urothelium consisting of 2-3 layers: a layer of basal cells (close arrow head), an intermediate layer of cells (arrow) and a superficial or apical layer composed of umbrella cells (open arrow head), a-h: Lp—connective mucosa, M—own muscular layer, Ur—urothelium.

Figure 16:
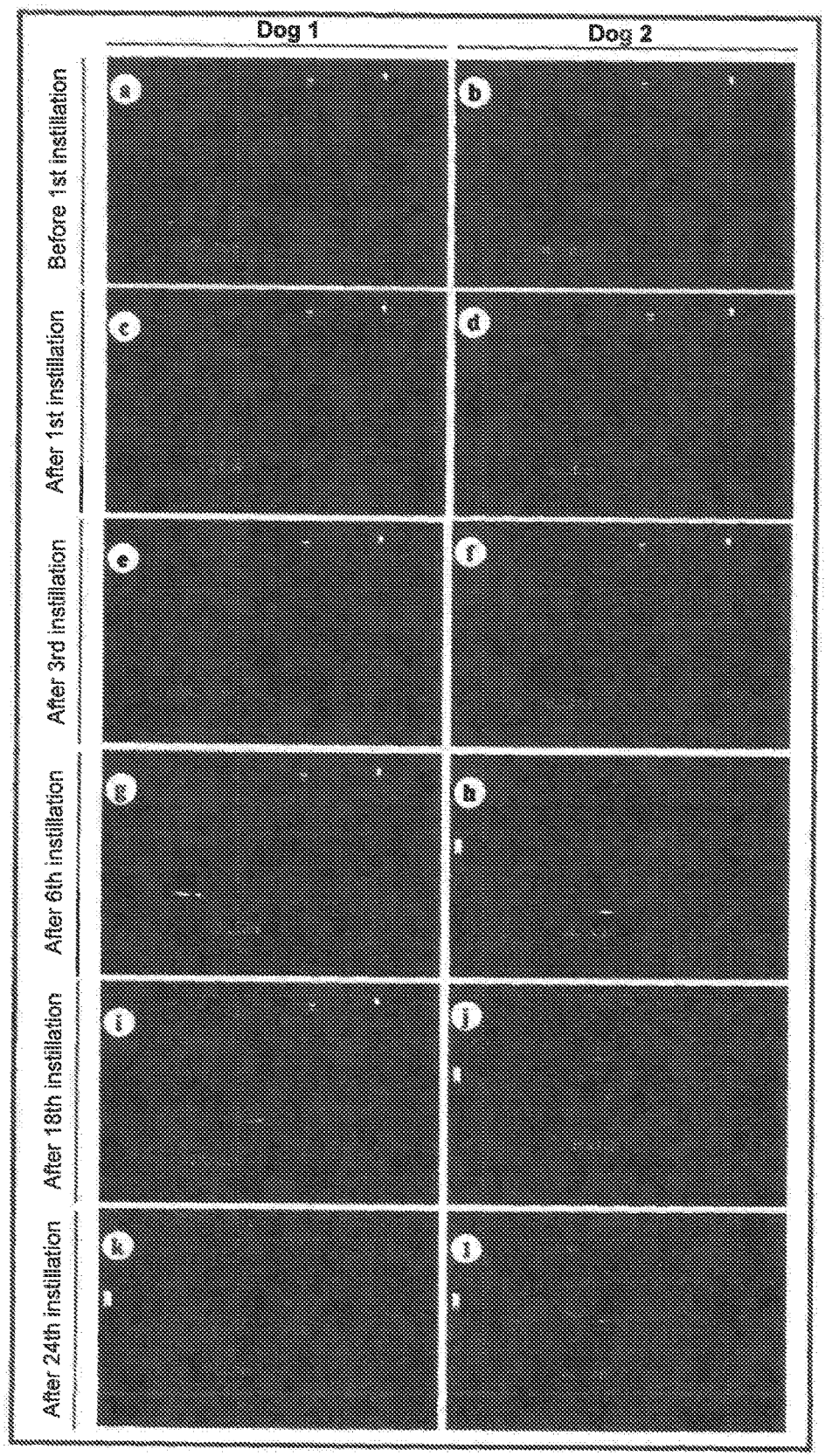

FIG. 16: Ultrasound representative of the urinary bladder of Dogs 1 and 2 in the following times: before the first instillation (a, b), after the first instillation (c, d) and after 3 (e, f), 6 (g, h), 18 (i, j) and 22 (k, l) instillations of MRB-CFI-1.

Figure 17:
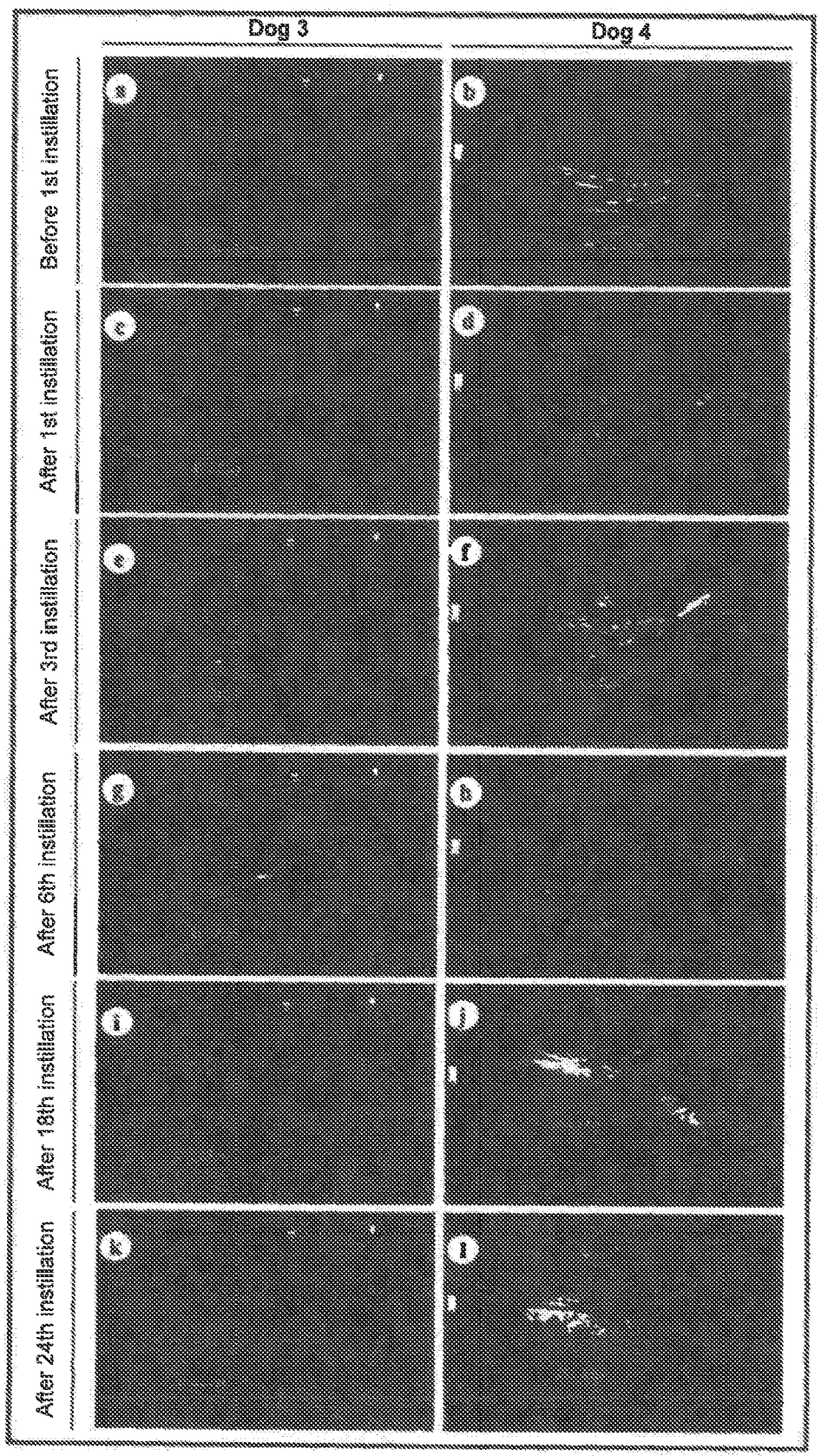

FIG. 17: Ultrasound representative of the urinary bladder of Dogs 3 and 4 in the following times: before the first instillation (a, b), after the first instillation (c, d) and after 3 (e, f), 6 (g, h), 18 (i, j) and 22 (k, l) instillations of MRB-CFI-3.

Figure 18:
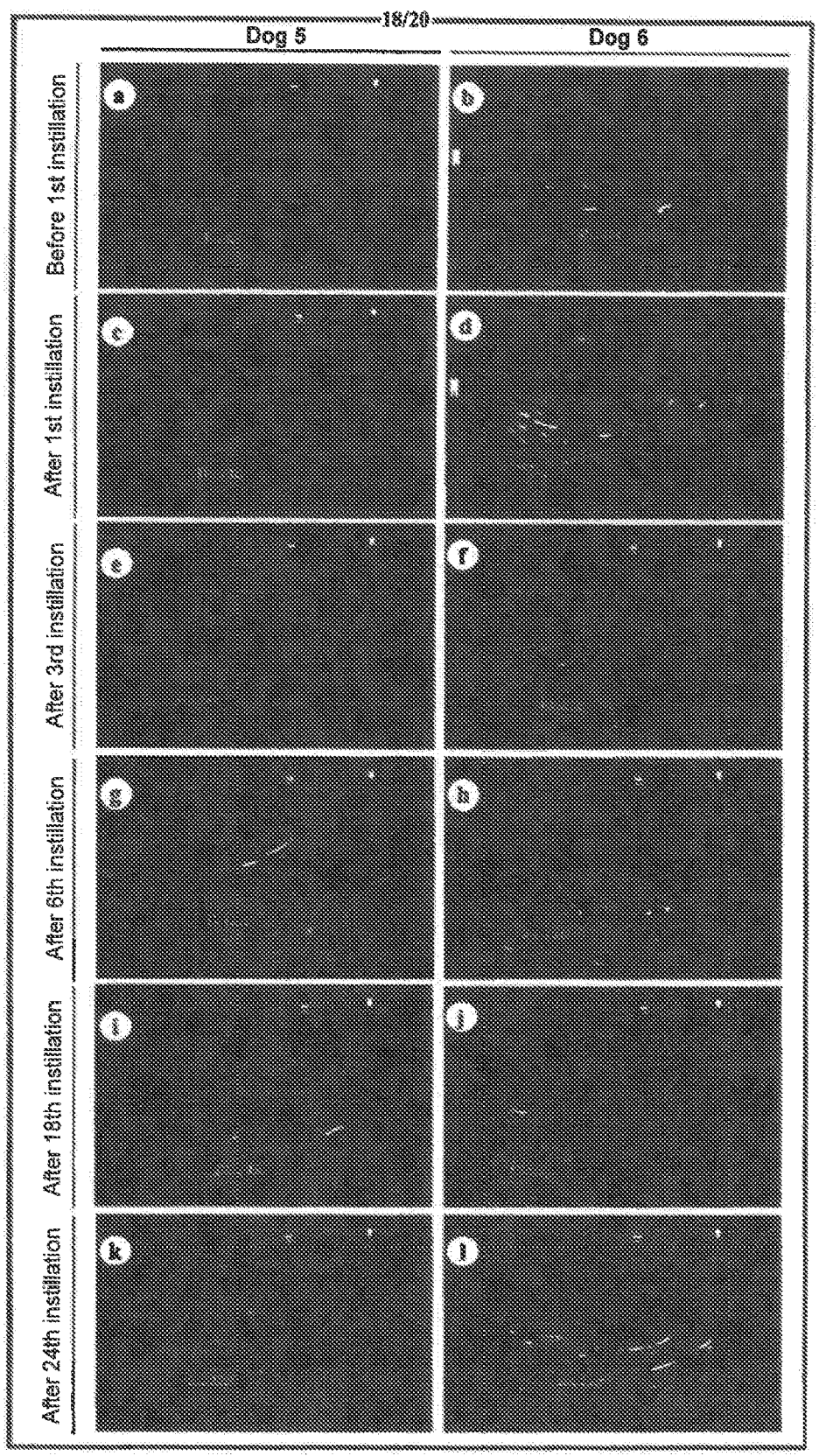

FIG. 18: Ultrasound representative of the urinary bladder of Dogs 5 and 6 in the following times: before the first instillation (a, b), after the first instillation (c, d) and after 5 (e, f), 6 (g, h), 8 (i, j) and 22 (k, l) instillations of MRB-CFI-5.

Figure 19:
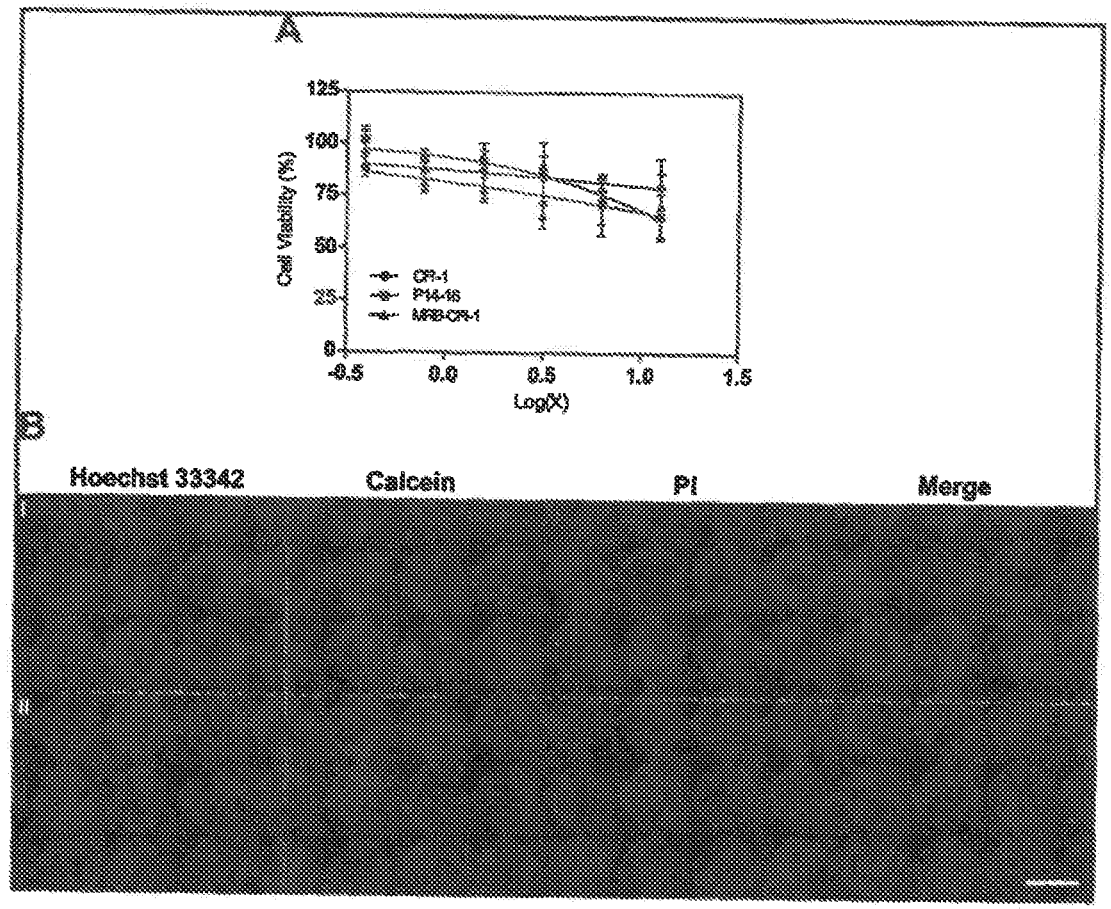

FIG. 19: Cytotoxicity of MRB-CFI-1 and 5637 cells of grade 11 urinary bladder carcinoma. (A) The 5637 cells were plated in a cell density of $2.0 \times 10^4$ and treated with serial dilutions of the compounds (12.5 mg, 6.25 mg, 3.13 mg, 1.56 mg and 0.39 mg) over 24 hours of incubation. Each value represents the mean±standard deviation of three independent experiments (n=3). Cell viability was normalized for untreated control. (B) Representative images of the MRB-CFI-1 compound by the calcein-AM/PI assay. The 5637 cells were plated in a cell density of $2.0 \times 10^4$ and treated with 12.5 mg, over 24 hours of incubation. The images were obtained with DAPI, GFP and propidium iodide, magnification of 100× and 2×2 stretching. Line: I—control group; II—12.5 mg MRB-CFI-1. Column: 1—Hoesch 33342 (DAPI); 2—Calcein (GFP); 3—Propidium iodide (PI), 4—Fusion of all channels. Bar scale: 300 pm.

Figure 20:
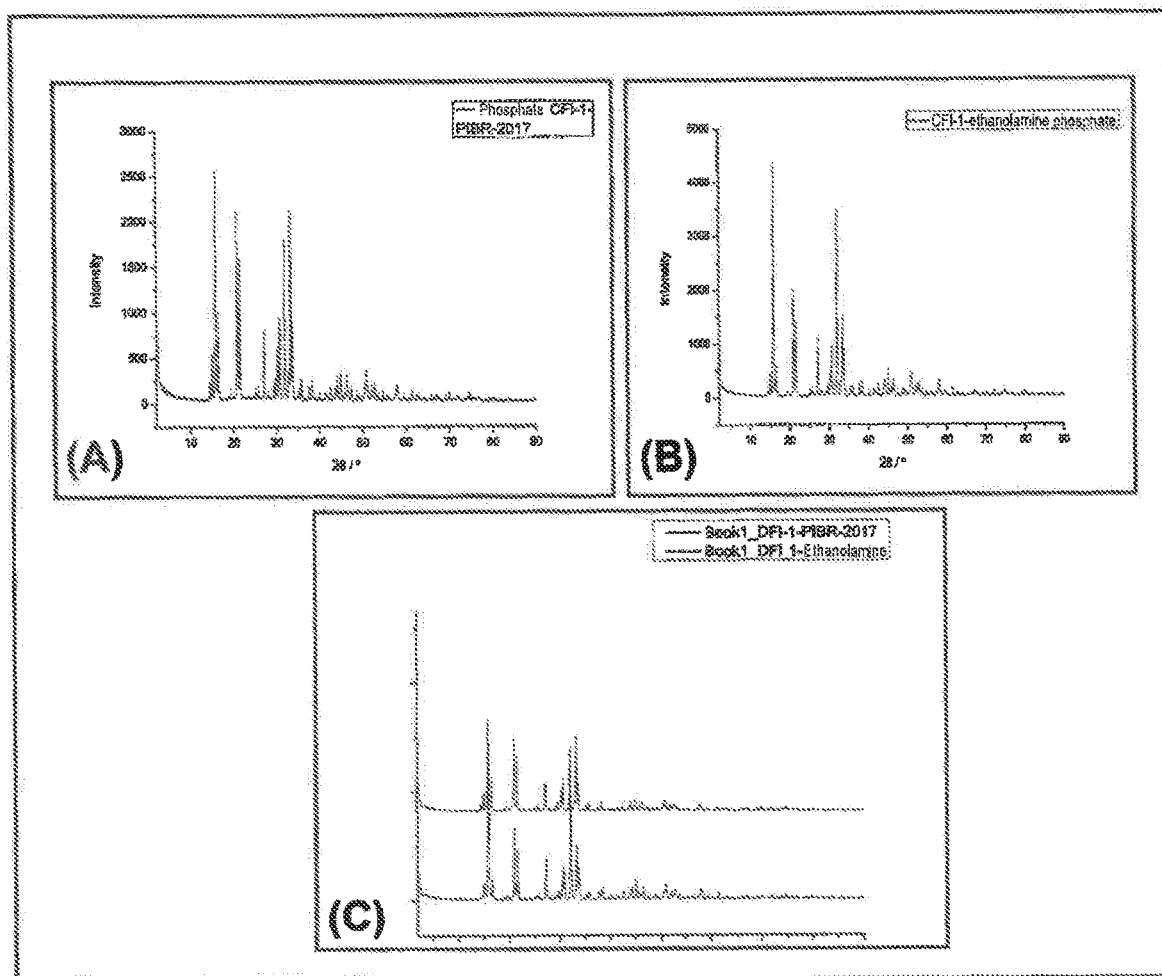

FIG. 20: X-ray diffraction (XRD): (A) CFI-1-PIBR-2017; obtained as defined in the example of embodiment (I). (B) CFI-1+ethanolamine; obtained as defined in the example of embodiment (II). (C) Superposition of the two XRD figures.

DETAILED DESCRIPTION OF THE INVENTION

In a first aspect, the present invention refers to processes of obtaining an inorganic nanostructured complex (CFI-1), a protein-associated nanostructured complex (MRB-CFI-1) and antitumor use.

Two examples of embodiments related to obtaining the inorganic nanostructured complex (CFI-1) and the protein-associated nanostructured complex (MRB-CFI-1) are described below.

Exemplary Embodiment (I)

The process of obtaining a nanostructured complex (CFI-1) by chemical synthesis comprises the following steps:

(a) Preparing dibasic ammonium phosphate [$(NH_4)_2HPO_4$] in situ in the presence of ammonia and orthophosphoric acid, in a mechanical homogenizer with minimum power of 500 W (for example, of the Ultra Turrax type), at a temperature between 25 and 55° C. for 20-30 min up to neutralization;

(b) Mixing two salts: Hexahydrate magnesium chloride, at 1-3% (by mass) and dibasic ammonium phosphate obtained in step (a) at 1-4% (by mass) between 22 and 30° C. and pH 5-7, in a mechanical homogenizer with minimum power of 500 W (e.g., of Ultra-Turrax type) in a variable rotation range between 7000 and 15000 rpm for 30-40 min;

(c) Applying a pressure level to the mixture obtained in step (b) in a high pressure homogenizer (e.g.; NIRO) with the homogenization valve with variable pressure between 400 and 700 bar, preferably 600 bar, and in the second stage, the homogenizing valve with variable pressure between 50 and 70 bar, preferably 60 bar, for up to 1 to 3 cycles, preferably 2 cycles;

(d) Cooling the suspension obtained at step (c) in ice bath at a temperature range comprised between 0 and 20° C., preferably 15° C.;

(e) Precipitating; and (f) Washing the crystals with distilled and sterile water and drying at 30 to 40° C., preferably at 37° C. for 24 to 72 h, preferably 48 h.

After step (f), the CFI-1 crystals were dried and weighed, showing a mass yield of 45-50%.

The nanostructured complex (CFI-1), obtained as defined in the embodiment example (I) (PRODUCT 1), comprises inorganic phosphate with size varying from 190.0 to 310.3±36.4 nm, polydispersity of 0.563 and zeta potential of −22.6+4.5 mV.

The process of obtaining a protein-associated nanostructured complex (MRB-CFI-1) by chemical synthesis comprises the following steps:

(a) Preparing dibasic ammonium phosphate [$(NH_4)_2HPO_4$] in situ in the presence of ammonia and orthophosphoric acid, in a mechanical homogenizer with minimum power of 500 W (for example, of the Ultra Turrax type), at a temperature between 25 and 55° C. for 20-30 min up to neutralization;

(b) Mixing two salts: Hexahydrate magnesium chloride, at 1-3% (by mass) and dibasic ammonium phosphate obtained in step (a) at 1-4% (by mass) between 22 and 30° C. and pH 5-7, in a mechanical homogenizer in a variable rotation range between 7000 and 15000 rpm for 30-40 min;

(c) Adding protein in a concentration of 0.5-1.5% (mass/mass), preferably 1%, to the complex obtained in step (b), wherein the aforementioned protein comprises the hydrolytic proteins selected from the group comprised by chitinase of *Bacillus subtilis* (14 kDa) and lysozyme from egg whites (14 kDa), preferably lysozyme, which have immunomodulatory activity.

(d) Applying a pressure level to the mixture obtained in step (c) in a high pressure homogenizer (NIRO) with the homogenization valve with variable pressure between 400 and 700 bar, preferably 600 bar, and in the second stage, the homogenizing valve with variable pressure between 50 and 70 bar, preferably 60 bar, for up to 1 to 3 cycles, preferably 2 cycles;

(e) Cooling the suspension obtained at step (c) in ice bath at a temperature range comprised between 0 and 20° C., preferably 15° C.;

(f) Precipitating; and (g) Washing the crystals with distilled and sterile water and drying at 30 to 40° C., preferably at 37° C. for 24 to 72 h, preferably 48 h.

The protein added in step (c) preferably comprises a concentration of 0.7%. The protein-associated nanostructured complex (MRB-CFI-1), obtained as defined in the example of embodiment (I), said PRODUCT 2, comprises inorganic phosphate associated with protein, with size varying from 318.0 to 477.1±146 nm, polydispersity of 0.9 and zeta potential of −28.60±6.74 mV.

Exemplary Embodiment (II)

The process of obtaining a nanostructured complex (CFI-1) by chemical synthesis comprises the following steps:

(a) Preparing an ultrapure (99.99%) dibasic ammonium phosphate [$(NH_4)_2HPO_4$] solution (molar mass: 132.6 g/mol) with concentration comprised in the range of 1 and 4% (by mass), preferably 1%, diluted in 1,000-2,000 mL of distilled water, under magnetic stirring with controlled speed and rotation between 200 and 400 rpm, preferably 300 rpm, at temperature between 22° C. and 30° C. and pH 8.26-8.57 for 5 minutes;

(b) Adding from 0.5 to 2.0% of an amine selected from the group comprised by monoethanolamine; diethanolamine and triethanolamine, preferably monoethanolamine (2-aminoethanol; $C_2H_7NO$; molar mass: 61.08 g/mol), in the solution of ammonium phosphate dibasic [$(NH_4)_2HPO_4$] obtained in step (a) under stirring, with rotation between 200 and 400 rpm, at a temperature range between 22° C. and 30° C., and pH between 9.72 and 9.80 for 5 minutes, until completing homogenization.

(c) Maintaining the solution of ammonium phosphate dibasic [$(NH_4)_2HPO_4$] and monoethalonamine, obtained in step (b), under mechanical stirring, rotation between 200 and 400 rpm, at temperature between 22° C. and 30° C. and pH 9.72-9.80;

(d) Preparing an ultrapure (99.99%) solution of hexahydrate magnesium chloride ($MgCl_2.6H_2O$) (molar mass: 203.3 g/mol), in a concentration comprised in the range of 1-3% (by mass), preferably 2%, under stirring with rotation comprised between 200 and 400 rpm, preferably 300 rpm, at the temperature range between 22 and 30° C., and pH between 7.38 and 7.56, for 5 min until completing homogenization; the solution is subsequently transferred into a 200-600 mL separation funnel or to a Titrette® Bottletop Burette apparatus with appropriate volume;

(e) Slow and controlled drip of the denser liquid obtained in step (d) in the resulting solution obtained in step (b) under stirring, with rotation between 200 and 400 rpm, at temperature between 22° C. and 30° C., and pH 9.72-9.80;

(f) Maintaining the solution resulting from step (e) under stirring for 2 hours with rotation between 200 and 400 rpm, at temperature between 22° C. and 30° C. and pH 8.10-8.20 until complete dissolution;

(g) Cooling the suspension obtained at step (f) in ice bath at a temperature range comprised between 0 and 20° C., preferably 15° C.;

(h) Precipitating;

(i) Washing the CFI-1 crystals with distilled and sterile water, and drying at 30 to 40° C., preferably at 37° C. for 24 to 72 h, preferably 48 h.

Drip control in step (e) is performed at the speed between 26 and 33 drops per minute, in a time interval between 3-4 hours.

The pH in step (e) is controlled so that 30 minutes after the start of dripping, the pH is comprised between 9.12 and 9.32; 1 hour after the start of dripping, the pH is comprised between 8.81 and 8.89; 2 hours after the start of dripping, the pH is comprised between 8.25 and 8.43; and 3 hours after the start of dripping, the pH is comprised between 8.10 and 8.20; the pH must be kept constant throughout the reaction.

After step (i), the CFI-1 crystals were dried and weighed, showing a mass yield of 98-100%.

The nanostructured complex (CFI-1) in the presence of a compound with an amine group that acts as pH stabilizer, obtained as defined in the embodiment of example (II), said PRODUCT 3, comprises inorganic phosphate with an average size of 449.6±116.6 nm, polydispersity of 0.55 and zeta potential of −20.0±5.1 mV.

The process of obtaining a nanostructured complex (CFI-1) associated with protein (MRB-CFI-1) in the presence of a compound with an amine group acting as a pH stabilizer comprises the addition of the CFI-1, obtained as defined in the example of embodiment (II), to a solid state protein, at 1:1, 1:2, 1:3 and preferably 1:2 weight/weight ratios, wherein the aforementioned protein is selected from the group comprised by P14-16, Bacillus subtilis chitinase (14 kDa) or egg white lysozyme (14 kDa), which are known to have immunomodulatory activities.

The protein-associated nanostructured complex P14-16 (MRB-CFI-1) comprises inorganic phosphate mixed with protein, by simple addition of protein crystals to CFI-1 at appropriate concentrations for the study of bladder cancer: with a mean size of 509.6±92.6 nm and zeta potential of −26.3±6.7 mV.

Further objects are the use of the complexes obtained (CFI-1) and (MRB-CFI-1) to treat cancer, preferably of prostate, bladder, colorectal, mastocytoma and lymphoma. Additionally, the complexes (CFI-1) and (MRB-CFI-1) can be used as adjuvants to commercial chemotherapeutic drugs to treat prostate, bladder, colorectal, mastocytoma and lymphoma cancers.

Although the compounds $NH_4MgPO_4 \times 6H_2O$, $(NH_4)_2MgH_2(PO_4)_2 \times 4H_2O$, $(NH_4)_2Mg_3(HPO_4)_4 \times 8H_2O$ and $NH_4MgPO_4 \times H_2O$ are described in the literature, associated or not with hydrolytic proteins, they are objects to treat cancer in this invention.

Results—Embodiment Example (I)

Characterization of the Nanostructured Magnesium and Ammonium Phosphate Complex (CFI-1):

Analysis of XFD shows the presence of ammonium, magnesium and phosphate: Table 1A (CFI-1) shows a ratio of phosphate to magnesium of 3.2 and shows only traces of metals, such as iron and calcium, and a value of the remaining structure, such as NH4+H2O (calculated by difference by weight of total mass). By this analysis, the approximate unit cell would be $(NH_4)_6Mg_3(PO_4)_4$. P/Mg ratio=3.2. Table 1B (MRB-CFI-1) shows a phosphate to magnesium ratio of 2.86. By this analysis, the unit cell is $(NH_4)_6Mg_3(PO_4)_4$, without considering the organic part.

TABLE 1A

Fluorescence X-ray analysis (XFD) of CFI-1:

| Analyte | Results (%) |
|---|---|
| $PO_4$ | 55.06 |
| Mg | 16.88 |
| Ca | 0.03 |
| Fe | 0.01 |
| $NH_4$ | 27.68 |
| Total | 99.66 |

Note:
The $NH_4$ value, in table 1A, shows a value associated with $H_2O$. The minimum chemical formula of these values was: $(NH_4)_6Mg_3(PO_4)_4$. $PO_4$/Mg ratio = 3.2

TABLE 1B

Fluorescence X-ray analysis (XFD) of MRB-CFI-1:

| Analyte | Results (%) |
|---|---|
| $PO_4$ | 50.47 |
| Mg | 17.62 |
| K | 1.41 |
| Na | 0.29 |
| Ca | 0.19 |
| Mn | 0.08 |
| Fe | 0.01 |
| Rb | 0.01 |
| $NH_4$ | 29.4 |
| Total | 99.98 |

Note:
$PO_4$/Mg ratio = 2.86. The minimum chemical formula of these values was: $(NH_4)_6Mg_3(PO_4)_4$, without considering the organic part.

Table 2 shows the components of the CFI-1 and MRB-CFI-1 complex on the surface of the crystals, such as magnesium, nitrogen, phosphorus and oxygen, and total absence of carbon by XPS. Therefore, this technique shows, on the crystal surface, nitrogen ($NH_4$), phosphate and magnesium as the only components of compound CFI-1. In the case of MRB-CFI-1, the protein components are shown. Therefore, for CFI-1 it would be $NO_6Mg_3(PO)_2$ and for MRB-CFI-1 it would be $C_{14}NO_8Mg_2(PO_4)_2$.

TABLE 2

Analysis of CFI-1 and MRB-CFI-1 by X-ray photoelectron spectroscopy (XPS) (%)

| | O | Mg | P | N | C | Na | K |
|---|---|---|---|---|---|---|---|
| CFI-1 | 60.3 | 19.1 | 16.4 | 4.2 | 0 | 0 | 0 |
| MRB-CFI-1 | 45.6 | 6.8 | 11.4 | 3.2 | 31.3 | 1.3 | 0.6 |

The minimum chemical formula of the crystal surface was as follows: for CFI-1: $NO_6Mg_3(PO_4)_2$ and for MRB-CFI-1: $C_{14}NO_8Mg_2(PO_4)_2$.

The crystal surface has the following values: CFI-1 ratio: P/Mg=0.86; MRB-CFI-1 ratio=P/Mg=1.68.

Figure 1:
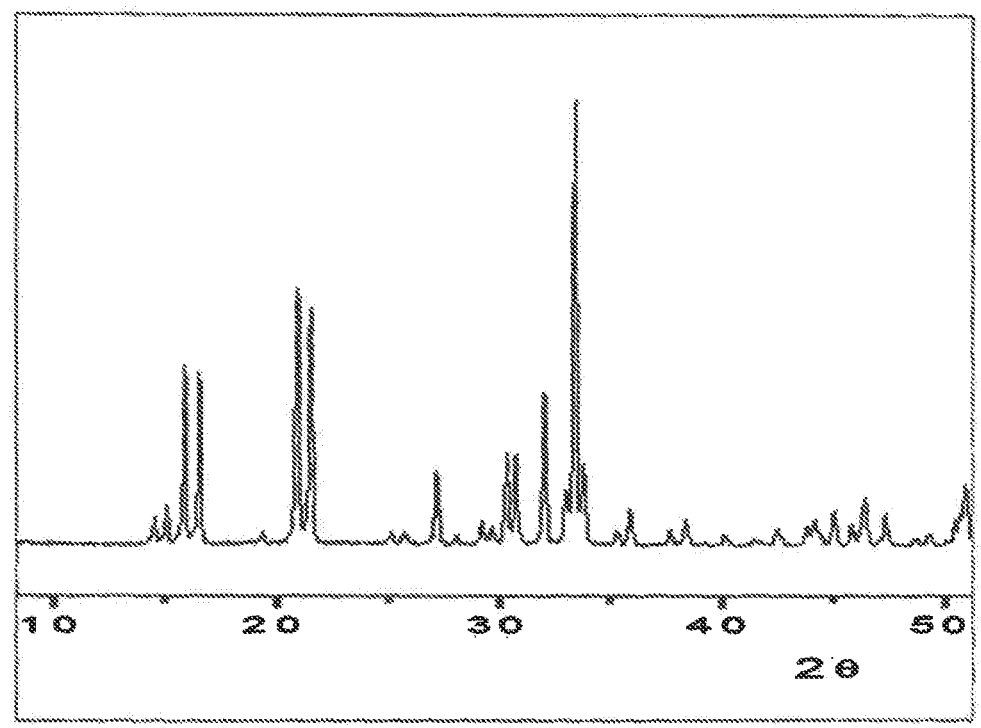
FIG. 1: X-ray diffraction pattern (XRD) of CFI-1.

X-Ray Refraction Pattern:

In FIG. 1, the diffraction of CFI-1 is similar to some of the salts of ammonium and magnesium phosphates; however, they differ in terms of intensities. Hence, they should have different distribution in the CFI-1 complex. There is an increase in face expression (022) and decrease of expression in faces [002], [111] and [211] relative to other phosphate salts. The phosphate/magnesium ratio of CFI-1 is 3.2, as demonstrated in the previous analysis. Hence, the unitary cell of the CFI-1 cluster presents a formula different from the other phosphate salts reported in the literature, besides that the CFI-1 is nanoparticulated, as it is shown in the following item. Nanocrystallization evidently indicates that the mineralized product was oriented along a specific direction of phases.

Fourier Transform Infrared Spectrum (FTIR):

The bands observed for CFI-1 (spectrum not shown in figure) around 3600, 3500, 3260 and 3115 $cm^{-1}$, in the FTIR spectrum, probably belong to the stretching vibrations of group OH and the antisymmetric stretching vibration of $NH_4$ groups. The water-$PO_4$—H bond appears around 2500 and 2200 $cm^{-1}$. Water deformation appears at 1680 $cm^{-1}$ and the bands at 1600 to 1400 $cm^{-1}$ were those of the deformation mode of the H—NH group of $NH_4$. The $PO_4$ group alone is observed at 1006 $cm^{-1}$ (antisymmetric elongation), 571 $cm^{-1}$ (P—O flexion), 463 and 438 $cm^{-1}$ ($PO_4^{-3}$ mode). At 618 and 688 $cm^{-1}$ (Mg—O bond), and at 894 $cm^{-1}$ the deformation bond of the group with Mg). The water-water hydrogen bond was observed at 760 and 695 $cm^{-1}$, while the bond between water hydrogen and $NH_4$ group was observed at 890 $cm^{-1}$. The MRB-CFI-1 FTIR spectrum presents the same bands with the addition of amide 11640-1650 $cm^{-1}$ and amide II 1574-1550 $cm^{-1}$ bands.

Figure 2:
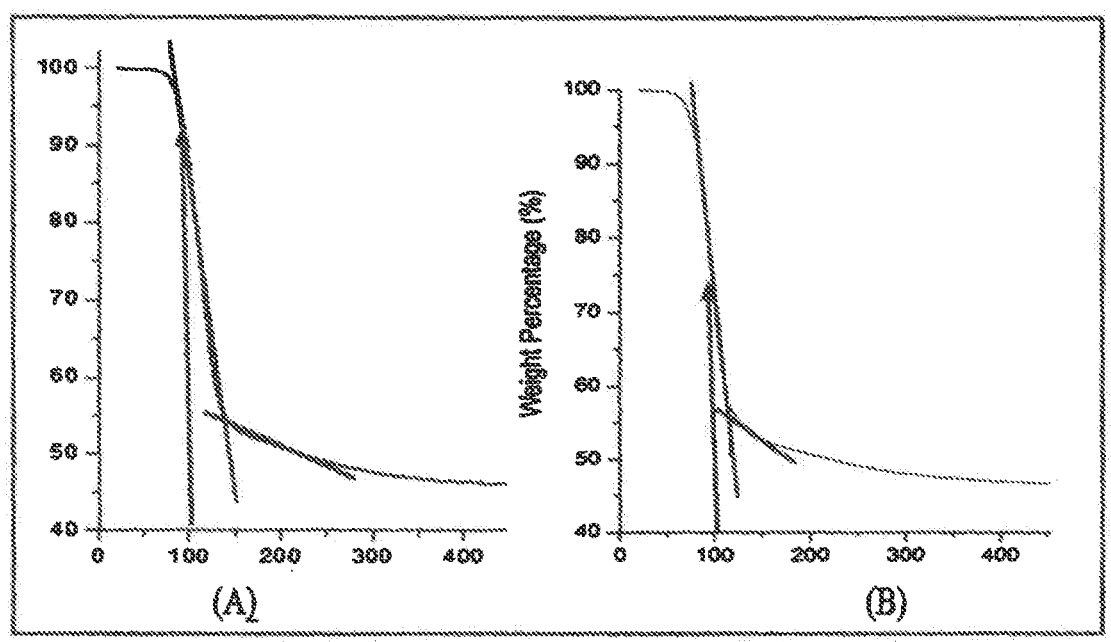
FIG. 2: Thermogravimetric analysis (TGA) of CFI-1 (A) and MRB-CFI-1 (B).

Thermogravimetric Analysis of CFI-1 and MRB-CFI-1:

FIG. 2A (CFI-1) shows weight loss at 100° C. of 8%, at 200° C. of 47%, at 250° C. of 50% and, at 350° C., loss of 53%. This shows loss of ammonia and water almost simultaneously. FIG. 2B showed weight loss at 100° C., 150° C., 200° C., 250° C. and 350° C. of 25%, 48%, 52%, 53% and 54%, respectively. Therefore, MRB-CFI-1 presented a faster weight loss than CFI-1, probably due to the presence of protein.

Figure 3:
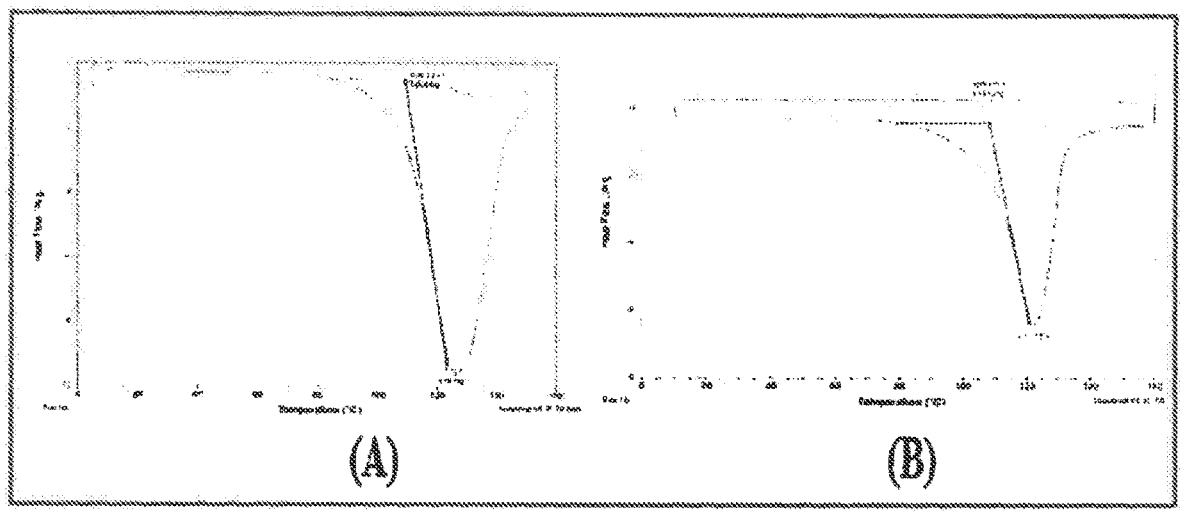
FIG. 3: Analysis of CFI-1 (A) and MRB-CFI-1 (B) differential scanning calorimetry (DSC). Speed of 10° C./min.

Differential Scanning Calorimetry (DSC) Analysis of CFI-1 and MRB-CFI-1:

FIG. 3A (CFI-1) shows the temperature on set: 109.1° C., the enthalpy (J/g), (ΔH°m) 1.262.00 J/g and melting point at 125,94° C. for CFI-1. FIG. 3B (MRB-CFI-1) shows the temperature onset: 108.1° C., the enthalpy (J/g) (ΔH°m) 1,311.00 J/g and MP=122.37° C. MRB-CFI-1 presents a melting point lower than the CFI-1 due to the presence of the protein.

Figure 4:
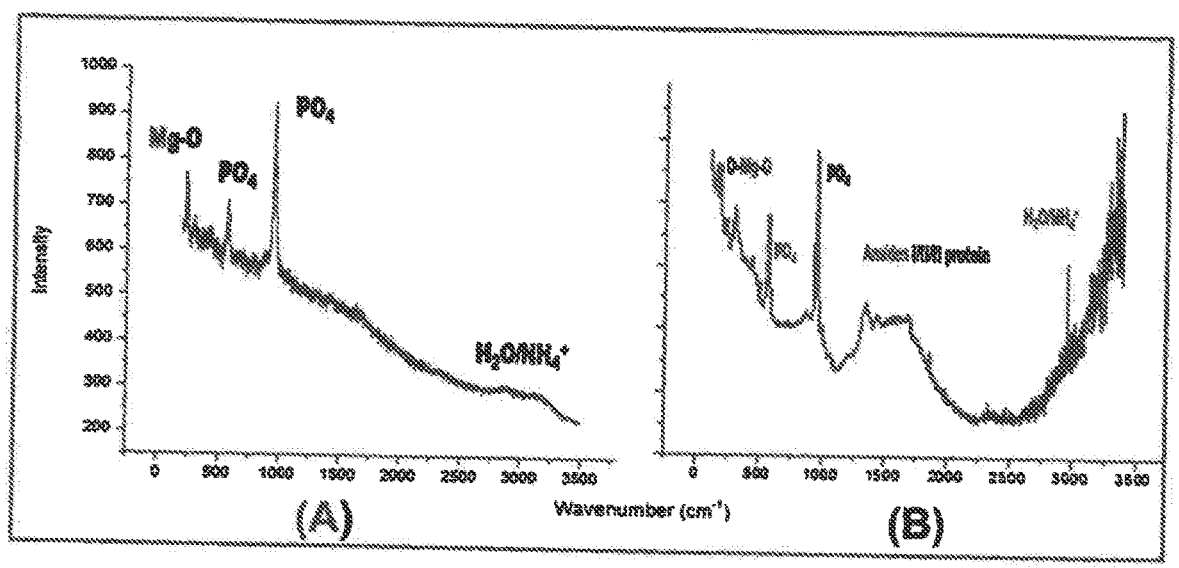
FIG. 4: Raman spectrum of CFI-1 (A) and MRB-CFI-1 (B).

Raman Spectrum:

FIG. 4A shows the Raman bands of CFI-1 observed at 189 and 296 $cm^{-1}$, which are designated respectively as the MgO strain vibration and the O—Mg—O deformation vibration. The band at 574 $cm^{-1}$ can be assigned to the v3 of $PO_4$ group. The 944 $cm^{-1}$ band can be assigned to the symmetrical stretching band of P—O group. In the wide wavelength region between 2670 and 3300 $cm^{-1}$ characteristics of vibration of strain vibration of $H_2O$ and $NH_4^+$ are found, and the small bands between 1400 and 1740 $cm^{-1}$ correspond to their deformation vibrations. FIG. 4B shows MRB-CFI-1 and all of these bands appeared corresponding to phosphates, magnesium and ammonium groups, concomitant with conventional Raman bands of amides between 1300-1650 $cm^{-1}$, corresponding to amides I, II and III, respectively. Size (nm) and surface charge (zeta potential, mV) of CFI-1:

FIG. 5A (CFI-1) shows a particle size value in the nano region of 190.0-310.3±36.4 nm. The zeta potential measured was −22.6±4.15 mV. FIG. 5B shows the MRB-CFI-1. Size ranging from 318.0 to 477.1±146 nm, polydispersity of 0.9 and zeta potential of −28.60±6.74 mV.

Solubility at Different pHs:

Table 3 shows the solubility of the CFI-1-water system that was determined at 25 and 35° C. by means of crystal and solution balance in a container. An experimental solution of 100 ml of volume containing 0.45 g of CFI-1 was treated at various pHs. The pH variation of the solution was made by the addition of HCl and NaOH solutions. The mixtures were continuously stirred for 24 h to ensure the solution saturation. The undissolved solid was settled without agitation and, after 2 additional hours, it was filtered through a 0.22 µm membrane filter. The residue was dried overnight in the oven at 35° C. The dry samples were weighed using an analytical balance. The difference between the residue and initial mass of CFI-1 provided the solubility. Table 3 shows that the solubility value at pH 7 was 80 mg/l. This value can change as a function of pH and ionic strength.

TABLE 3

Solubility of CFI-1 at different pHs [0.45 g/100 ml CFI-1].

| pH | Solubility by weight difference (mg/L) | |
|---|---|---|
| | 25° C. | 35° C. |
| 7.0 | 180 | 250 |
| 5.0 | 270 | 285 |
| 3.0 | 300 | 325 |

Characterization of MRB-CFI-1 Complex:

X-Ray Diffraction Pattern (XRD).

Figure 5:
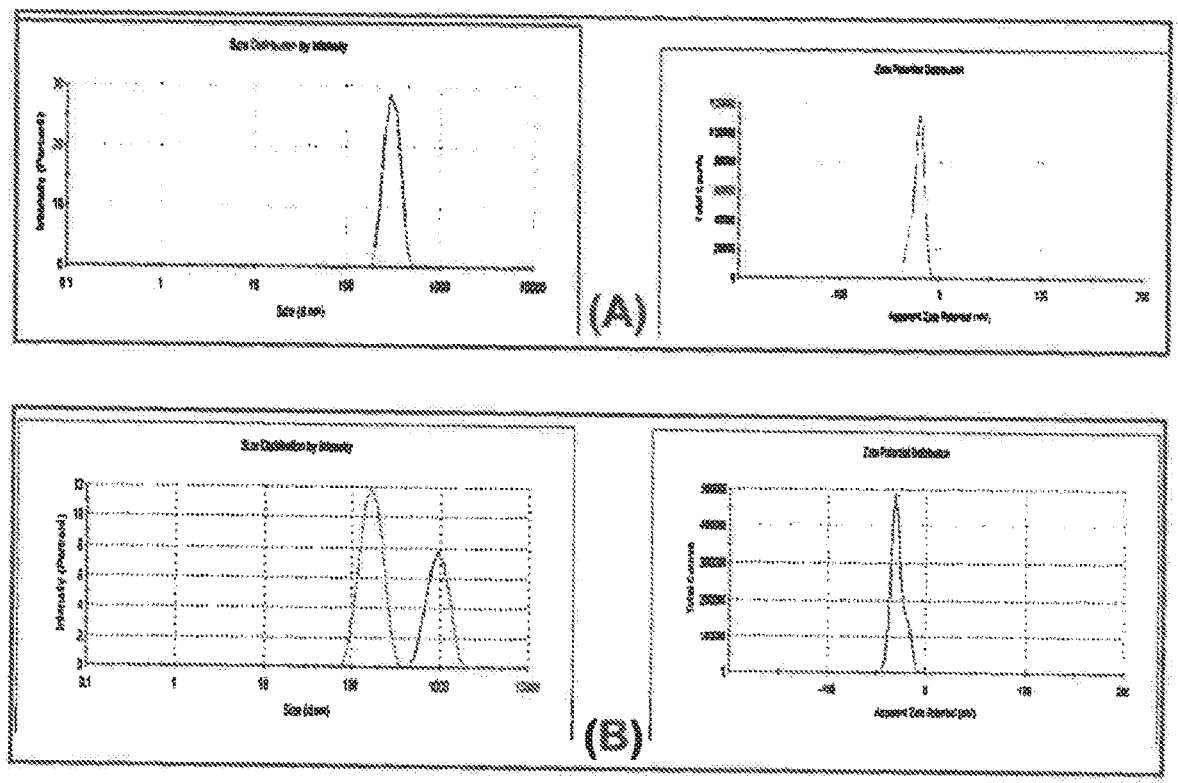
FIG. 5: Size and surface charge of CFI-1 (A) by dynamic light scattering method (DLS) or photon correlation spectroscopy (PCS) by intensity. Zeta potential measured by electrophoretic mobility in Zeta Sizer (MALVEM). (B) shows the same method applied to MRB-CFI-1.
Figure 6:
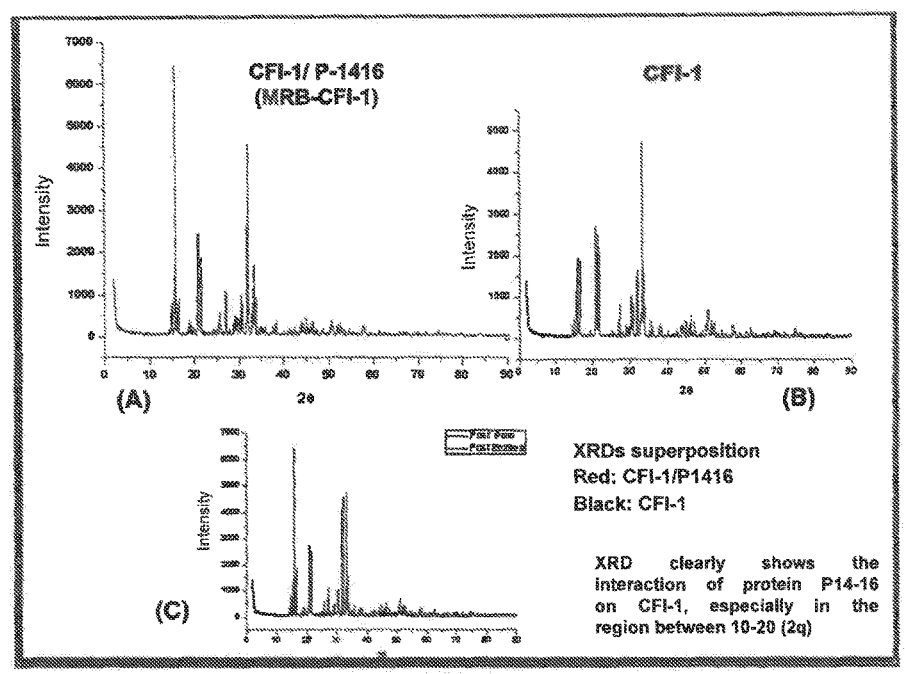
FIG. 6: MRB-CFI-1 (A) and CFI-1 (B) X-ray diffraction pattern. (C) Superposition of CFI-1 and MRB-CFI-1 standards.

FIG. 6 clearly shows the association of CFI-1 with lysozyme protein (P14-16). The superpositions of the two diffractions differ in some of the 2θ values. FIG. 5 shows that the product obtained in the presence of P 14-16 protein had a higher expression of diffraction on faces (002) and (120), indicating that the mineralization product was preferably oriented in a single direction. This shows a strong interaction of the protein P14-16 in relation to CFI-1.

Circular Dichroism of MRB-CFI-1.

Figure 7:
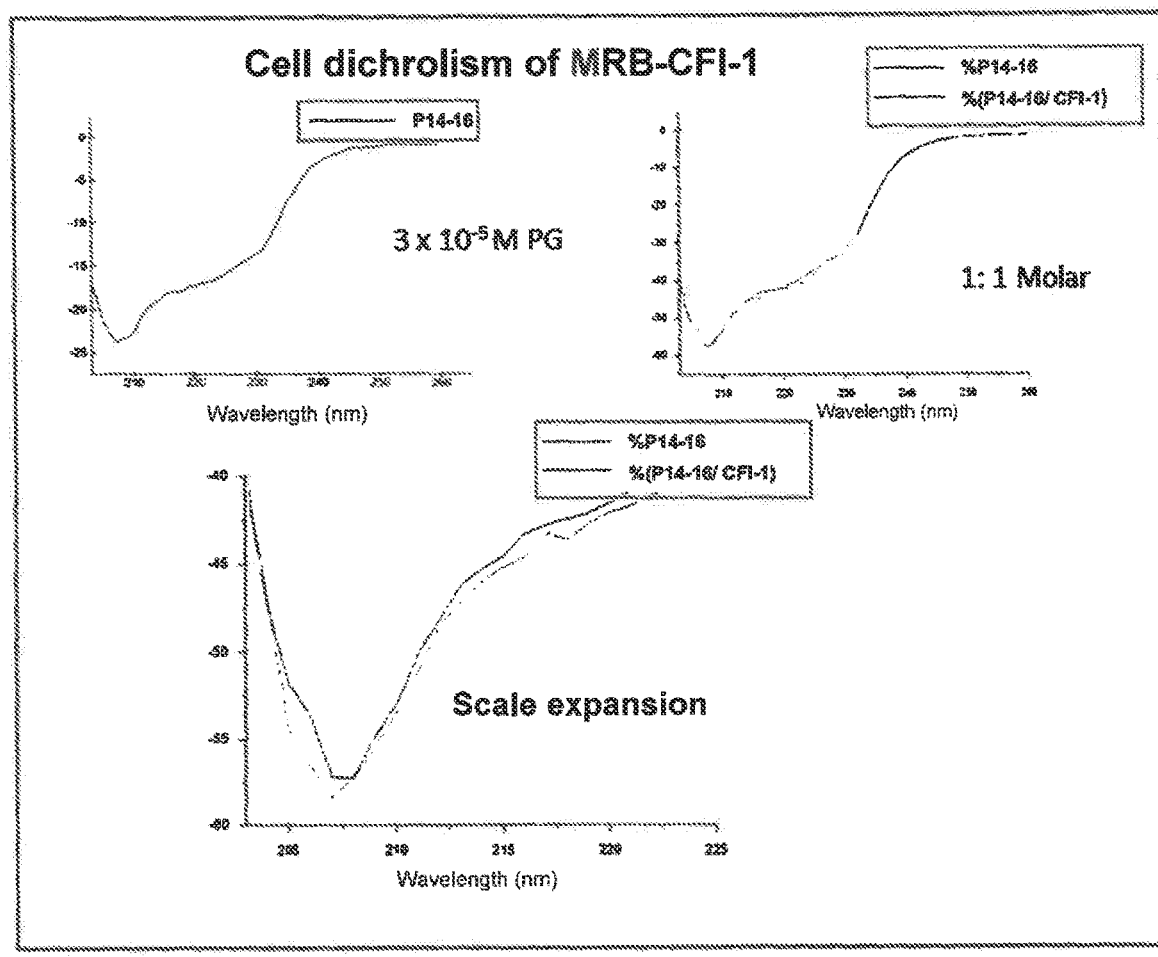
FIG. 7: Circular dichroism (CD) of CFI-1 and CFI-1 associated with P14-16 protein (or MRB-CFI-1).

FIG. 7 shows in the UV 200-250 nm region, the magnitude of the ellipticity at 208 nm and 222 nm, where there was a variation for MRB-CFI-1 complex at pH 7.4 (PBS). The increase indicated an increase in the alpha-helix content of the native P14-16 protein (lysozyme). This increase of alpha-helix content indicates a more orderly structure, since some of the residues should be involved in the interaction in the non-helical region of the tertiary structure. This type of effect occurs in proteins when they undergo the action of negative surfactants. In this case, the CFI-1, that is negative, shows the same effect.

Size (Nm) and Surface Charge (Zeta Potential, mV) of CFI-1 (A) Versus (B) MRB-CFI-1.

Figure 8:
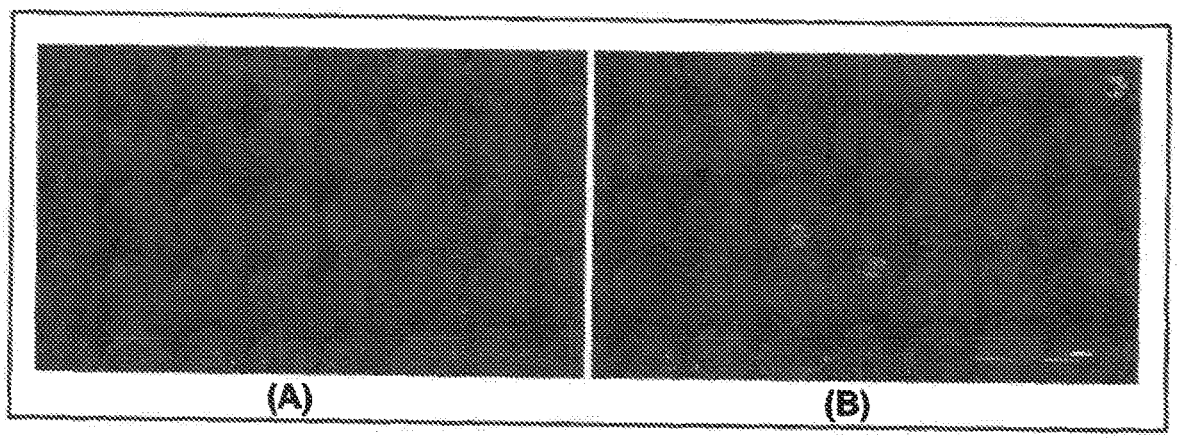
FIG. 8: Emission field scanning microscopies (FESEM micrograph) for CFI-1 (A) and MRB-CFI-1 (B), agree with the size measured by the dynamic light scattering method (DLS) described in FIG. 5.

FIG. 8 showed a comparison of the different distribution when CFI-1 is associated with P14-16 protein (MRB-CFI-1). MRB-CFI-1 (FIG. 8B) shows lower homogeneity than CFI-1 alone (FIG. 8A). MRB-CFI-1 shows a small increase in particle size and surface charge (FIG. 5). Their analyses by FESEM clearly show the spherical and nanometric characteristics of both the CFI-1 (FIG. 8C) and MRB-CFI-1 (FIG. 8D).

In Vivo Toxicological and Biochemical Analyses of MRB-CFI-1:

For the toxicological and biochemical analyses of the nanodrug MRB-CFI-1, 20 Fischer 344 female rats, 20 C57BL/6 female mice and 20 New Zealand female rabbits were used.

The animals were distributed into 4 groups for each species, namely: control group (n=5 animals for each species): received an intravesical dose of physiological solution 0.9%, for 6 consecutive weeks; group MRB-CFI-1 20 (n=5 animals for each species): received an intravesical dose of MRB-CFI-1 20 mg/Kg for 6 consecutive weeks; group MRB-CFI-1 50 (n=5 animals for each species): received an intravesical dose of MRB-CFI-1 50 mg/Kg for 6 consecutive weeks; group MRB-CFI-1 100 (n=5 animals for each species): received an intravesical dose of MRB-CFI-1 100 mg/Kg for 6 consecutive weeks.

The protocol for use of animals in research was approved by the Ethics Committee on the Use of Animals (CEUA)—UNICAMP (protocols numbers: 4536-1/2017; 4579-1/2017; 4435-1).

After the 6-week experimental period, all animals from each group were euthanized. For the local and systemic toxicity analyses of the MRB-CFI-1 nanodrug, the organs of the urinary system (urinary bladder, ureters and kidneys), and other target organs such as liver, spleen, stomach and pancreas, were collected and subjected to histopathological analyses. The histopathology of these organs was evaluated and the toxicity correlated with the degrees of inflammation. The degree of inflammation was evaluated by a semi-quantitative scale: 0, absence of inflammation, 1, minimal inflammation (less than five lymphocytes in an area of 0.25 $mm^2$), 2, moderate inflammation (mononuclear inflammatory cells scattered throughout the tissue, but still with visible stroma), 3, intense inflammation (mononuclear inflammatory cells densely infiltrating the tissues.

Also, biochemical analyses were performed to verify the systemic toxicity of this compound, namely: alanine aminotransferase (ALT), a specific marker for hepatic parenchymal lesion; aspartate aminotransferase (AST), a nonspecific marker for hepatic and/or cardiac injury; alkaline phosphatase; as well as circulating levels of creatinine and urea to verify renal function. Spectrophotometric determinations were performed on a Pharmacia Biotech spectrophotometer with a temperature-controlled cuvette chamber (UV/visible Ultrospec 5,000 with Swift II application software for computer control, 97-4213, Cambridge, England, UK). All chemical reagents were from company LaborLab (Guarulhos, Sao Paulo, Brazil).

In Vivo Assessment of Peritoneal Inflammatory Response after Administration of CFI-1, P14-16 Protein and MRB-CFI-1 Compound:

To verify whether compound MRB-CFI-1 and its constituents (CFI-1 and P14-16 protein) were able to deflate the peritoneal inflammatory response (activation of the immune system) when administered directly to the abdominal cavity, 8 7-week old Fischer 344 female rats were used, weighing 150 grams on average, which were obtained at the Vivarium Center of the State University of Campinas (CEMIB/UNICAMP).

The animals were divided into 4 groups (n=2 animals per group): Control group: received an intraperitoneal dose of 0.3 mL of physiological solution 0.9% every 72 hours, totaling 3 doses; group CFI-1: received an intraperitoneal dose of 20 mg/kg of CFI-1 suspended in physiological solution 0.9% every 72 hours, totaling 3 doses; group P14-16: received an intraperitoneal dose of 20 mg/Kg of protein P14-16 suspended in physiological solution 0.9% every 72 hours, totaling 3 doses; group MRB-CFI-1: received an intraperitoneal dose of 20 mg/kg of compound MRB-CFI-1 suspended in physiological solution 0.9% every 72 hours, totaling 3 doses. After 24 hours from the last application of each compound, the animals were euthanized and the peritoneums were evaluated macroscopically and collected for further histological assessment.

The protocol for use of animals in research was approved by the Ethics Committee on the Use of Animals (CEUA)—UNICAMP (protocol number: 4536-1/2017).

Pre-Clinical Trial: Induction and Treatment of Non-Muscle Invasive Urinary Bladder Cancer (NMIBC) in Fischer 344 Rats:

In the present invention, 100 7-week Fischer 344 rats were used, weighing 150 grams on average, which were obtained from the Vivarium Center of the State University of Campinas (CEMIB/UNICAMP). For NMIBC induction, 80 animals were anaesthetized with xylazine hydrochloride 2% (5 mg/kg i.m.; Köig, Sao Paulo, Brazil) and ketamine hydrochloride 10% (60 mg/kg, i.m.; Fort Dodge, Iowa, USA), maintained in this state for 45 minutes to avoid spontaneous urination and a dose of 1.5 mg/kg of N-methyl-N-nitrosourea (MNU-Sigma, St. Louis, Mo., USA) dissolved in 0.3 ml of sodium citrate (1M pH 6.0) was instilled every 15 days (weeks 0, 2, 4 and 6), totaling 4 doses (Fávero et al., 2014; Garcia et al., 2016). The other 20 animals that did not receive MNU were considered as the control group.

Two weeks after the last MNU dose, the animals were submitted to an ultrasound examination to evaluate tumor occurrence. Ultrasounds were evaluated using a portable software-controlled ultrasound system with a 10-5 MHz 38 mm linear transducer.

Figure 9:
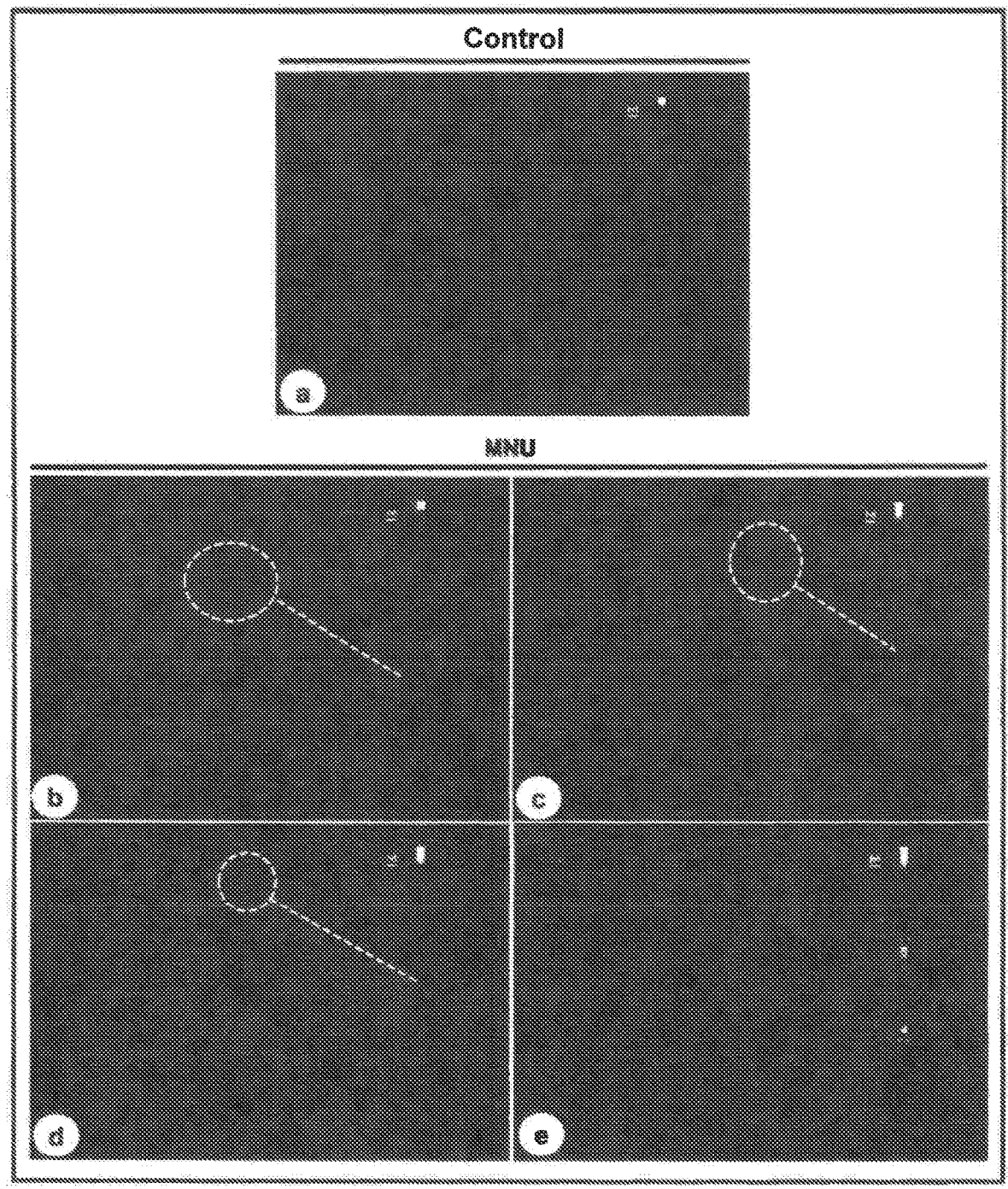
FIG. 9: Ultrasonography of the animals from control group (a) and induced with MNU (b, c, d, e). (a) Urinary bladder morphology with normal aspects (a), (b) Tumor masses infiltrating the cranial, ventral and dorsal walls of the bladder, measuring 0.32 cm×0.21 cm (b), 0.32 cm×0.24 cm (c) and 0.27 cm×0.21 cm (d). Color Doppler mapping showing intense blood flow inside the tumor mass (e).
Figure 10:
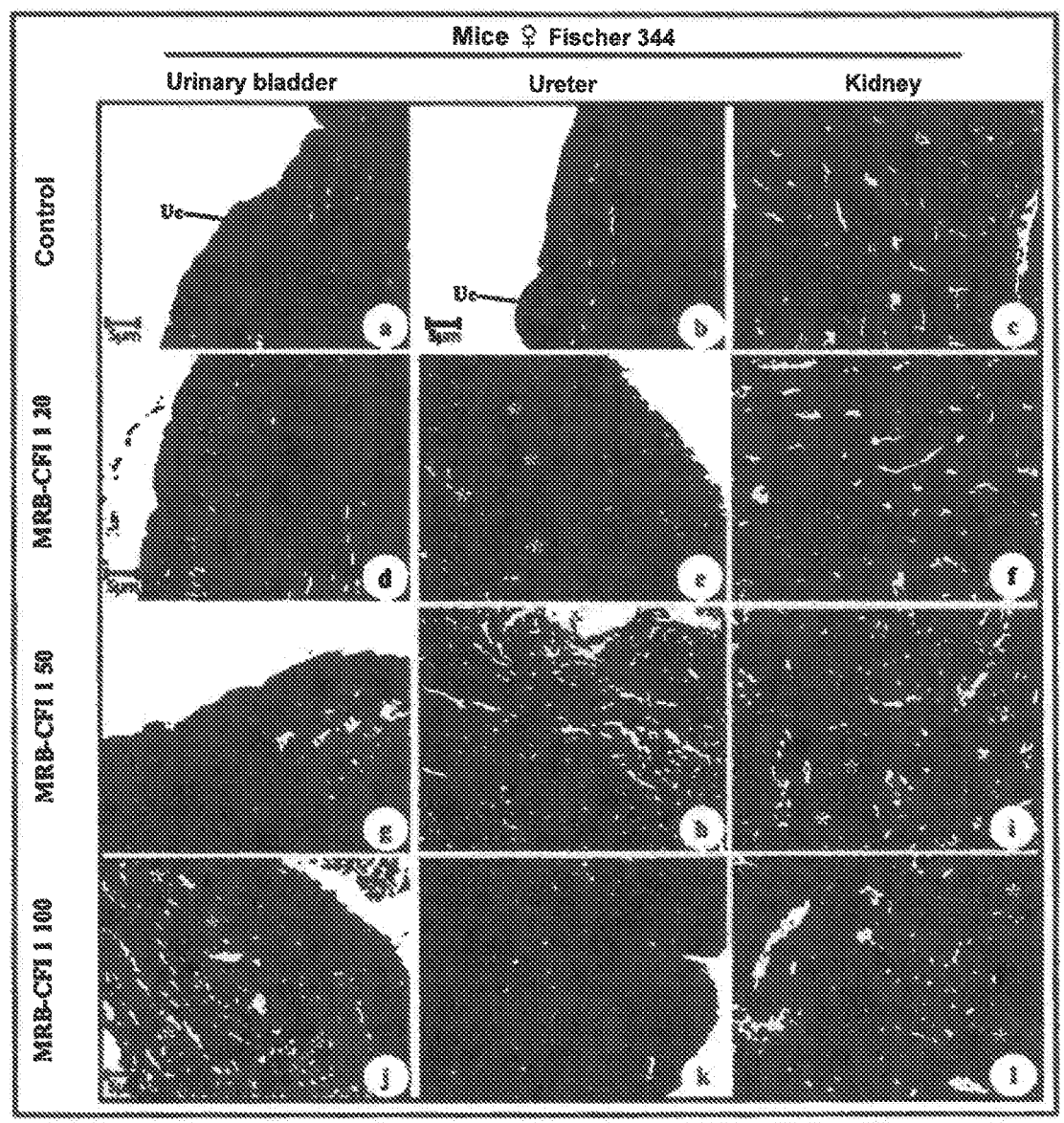
FIG. 10: Photomicrographies of the urinary bladder, ureter and kidney of rats in the control group (a, b, c); MRB-CFI1 20 (d, e, f); MRB-CFI1 50 (g, h, i); and MRB-CFI1 100 (j, k, l). (a) and (b) normal urothelial composed of 2-3 cell layers: one layer of basal cells (Bc), one layer of intermediate cells (Ic), and one superficial layer composed of umbrella cells (UC). (c) and (f) Normal nephrons: glomeruli (Gl), podocytes (Pd), proximal contorted tubule (Pct), distal contorted tubule (DCT), macula densa (Md), urinary pole (Up) and vascular pole (Vp). (j) and (k) flat urothelial hyperplasia and intense inflammation (asterisks and arrows), both in the urinary bladder and in the ureter; blood vessel (By). (l) Intense inflammation (asterisks) in the nephrons. (d) and (e) Minimal inflammation (asterisks and arrows) both in the urinary bladder and in the ureter, (g) and (h) moderate inflammation (asterisks and arrows) and flat urothelial hyperplasia in both the urinary bladder and the ureter, (i) moderate inflammation (asterisks) in the nephrons. a-l: Gl—glomerulus, Lp—lamina propria, Ur—urothelium.

Ultrasound of the urinary bladder of the animals induced with MNU showed tumor masses infiltrating the cranial, ventral and dorsal walls of the organ, measuring 0.32 cm×0.21 cm; 0.32 cm×0.24 cm; and 0.27 cm×0.21 cm (FIGS. 9b, 9c and 9d). Color Doppler mapping evidenced intense blood flow inside the tumor masses, reinforcing the diagnosis of urothelial neoplasia (FIG. 9e).

After NMIBC induction with MNU, the animals were distributed into 5 groups (20 animals per group): control group (group 1): received an intravesical dose of 0.3 ml of physiological solution 0.9% for 6 consecutive weeks; group MNU (cancer, group 2): received the same treatment as group 1; group MNU+CFI-1 (group 3): received an intravesical dose of 20 mg/kg of CFI-1 suspended in physiological solution 0.9% for 6 consecutive weeks; group MNU+P14-16 (group 4): received an intravesical dose of 20 mg/kg of protein P14-16 suspended in physiological solution 0.9% for 6 consecutive weeks; group MNU+MRB-CFI-1 (group 5): received an intravesical dose of 20 mg/Kg of compound MRB-CFI-1 suspended in physiological solution 0.9% for 6 consecutive weeks.

The intravesical doses in the different experimental groups were instillated using a 20 gauge flexible catheter (Abocath, Sao Paulo, Brazil). The animals from all experimental groups received water and the same solid diet ad libitum (Nuvilab, Colombo, PR, Brazil). After 16 weeks of treatment, the animals were euthanized and the urinary bladders were collected and subjected to histopathological and immunohistochemical analyses. The protocol for use of animals in research was approved by the Ethics Committee on the Use of Animals (CEUA)—UNICAMP (protocol number: 4536-1/2017).

Histopathologic Analysis:

For histological analysis, samples of the urinary bladder from all animals of each experimental group (n=20 animals per group) were collected and fixed with Bouin for twelve hours. After fixation, tissues were washed in ethyl alcohol 70%, with subsequent dehydration in a growing series of alcohols. Subsequently, the fragments were cleared with xylene for 2 hours and included in plastic polymers (Paraplast Plus, ST. Louis, Mo., USA). Subsequently, the materials were sectioned using a Slee CUT5062 RM 2165 microtome (Slee Mainz, Mainz, Germany) with 5 micrometer thickness, stained with hematoxylin-eosin and photographed using DM2500 photomicroscope (Leica, Munich, Germany).

The diagnosis of urothelial lesions was classified according to the staging proposed by the common understanding of the World Health Organization/International Society of Urological Pathology (Epstein et al., 1998).

Antigen immunostaining: TLR4, TRIF, IRF3, INF-γ, TLR2, IKK-α, MyD88, IL-6 and TNF-α:

Samples from the urinary bladder of all animals of each experimental group (n=20 animals per group), the same used for histopathological analyses, were used for immunostaining. Then, cuts with 5 μm thickness in the rotating microtome Slee CUT5062 RM 2165 (Slee Mainz, Mainz, Germany) were collected on silanized sections. The antigenic recovery was performed by incubation of the sections in citrate buffer (pH 6.0) at 100° C. in a microwave, or by treatment with proteinase K, depending on the characteristics of each antibody. The blockage of endogenous peroxidases was carried out with $H_2O_2$ (methanol 0.3%) with subsequent incubation in a blocking solution with bovine serum albumin (BSA) 3%, in TBS-T buffer for 1 hour at room temperature. Subsequently, the antigens TLR4, TRIF, IRF3, INF-γ, TLR2, IKK-α, MyD88, IL-6 and TNF-α were located through the specific primary antibodies (table 4), diluted in BSA 1% and stored overnight at 4° C. The Advance™ HRP kit (Dako Cytomation Inc., USA) was used for antigen detection according to the manufacturer instructions. After washing with TBS-T buffer, the cuts were incubated with conjugated secondary HRP antibody from the Advance™ HRP kit for 40 minutes, and were subsequently revealed with diaminobenzidine (DAB), counterstained with Harris hematoxylin and evaluated using a DM2500 photomicroscope (Leica, Munich, Germany).

To evaluate the immunoreactivity intensity of the antigens, the percentage of positive urothelial cells was examined in ten fields for each antibody with a 400× magnitude. The staining intensity was graded on a 0-3 scale, and expressed as 0 (absence of immunoreactivity), 0% of positive urothelial cells; 1 (weak immunoreactivity), 1-35% of positive urothelial cells; 2 (moderate immunoreactivity), 36-70% of positive urothelial cells; and 3 (intense immunoreactivity), >70% of positive urothelial cells (Garcia et al., 2016).

TABLE 4

Characteristics of the primary antibody for immunostaining.

| Primary antibodies | Host species | Code | Source |
|---|---|---|---|
| TLR2 | Rabbit (policlonal) | ABBI-251110 | Abbiotec, USA |
| TLR4 | Rabbit (policlonal) | ABBI-251111 | Abbiotec, USA |
| IKK-α | Rabbit (policlonal) | sc-7218 | Santa Cruz Biotechnology, CA, USA |
| MyD88 | Rabbit (policlonal) | ab38515 | abcam, USA |
| IL-6 | Rabbit (policlonal) | ab83339 | Abcam, EUA |
| TNF-α | Rabbit (policlonal) | ab6671 | abcam, USA |
| TRIF | Rabbit (policlonal) | ab13810 | Abcam, Cambridge, MA, USA |

TABLE 4-continued

Characteristics of the primary antibody for immunostaining.

| Primary antibodies | Host species | Code | Source |
|---|---|---|---|
| IRF3 | Rabbit (policlonal) | ab25950 | Abcam, Cambridge, MA, USA |
| INF-γ | Mouse (monoclonal) | 507802 | Biolegend, USA |

Statistical Analysis:

The histopathological and immunohistochemical analyses were evaluated using the ratio test. For these analyses, a 5% type I error was considered statistically significant.

Pre-Clinical Trial: Induction and Treatment of Non-Muscle Invasive Urinary Bladder Cancer (NMIBC) in C57BL/6 Mice:

In the present invention, 100 7-week old C57BL/6J female mice were used, weighing 40 grams on average, which were obtained from the Vivarium Center of the State University of Campinas (CEMIB/UNICAMP). The animals from all experimental groups received water and the same solid diet ad libitum (Nuvilab, Colombo, PR, Brazil). For NMIBC induction, 80 animals were anaesthetized with xylazine hydrochloride 2% (5 mg/kg i.m.; König, Sao Paulo, Brazil) and ketamine hydrochloride 10% (60 mg/kg, i.m.; Fort Dodge, Iowa, USA), maintained in this state for 45 minutes to avoid spontaneous urination and a dose of 1.5 mg/kg of N-methyl-N-nitrosourea (MNU-Sigma, St. Louis, Mo., USA) dissolved in sodium citrate (1M pH 6.0) was instilled every 15 days (weeks 0, 2, 4 and 6), totaling 3 doses (Fávero et al., 2012). The other 20 animals that did not receive MNU were considered as the control group.

One week after the last MNU dose, the animals were submitted to ultrasound examination to evaluate tumor occurrence and were subsequently divided into 5 groups (n=20 animals per group) for the respective treatments: a) control group (group 1): received a intravesical dose of 0.1 ml of physiological solution 0.9% for 6 consecutive weeks; b) MNU Group (cancer): received the same treatment as group 1; c) MNU+CFI-1 group (group 3): received an intravesical dose of 20 mg/Kg of inorganic phosphate (CFI-1) for 6 consecutive weeks; d) MNU+P14-16 group (group 4): received an intravesical dose of 20 mg/kg of P14-16 protein for 6 consecutive weeks; e) MNU+MRB-CFI-1 group (group 5): received an intravesical dose of 20 mg/kg of MRB-CFI-1 compound for 6 consecutive weeks.

The intravesical doses in the different experimental groups were instillated using a 22 gauge flexible catheter (Abocath, Sao Paulo, Brazil). Urine was collected weekly and, after treatment, the animals were euthanized and the urinary bladders were collected. The protocol for use of animals in research was approved by the Ethics Committee on the Use of Animals (CEUA)—UNICAMP (protocol number: 4579-1/2017).

Histopathologic Analysis:

For histological analysis, samples of the urinary bladder from all animals of each experimental group (n=20 animals per group) were collected and fixed with Bouin for twelve hours. After fixation, tissues were washed in ethyl alcohol 70%, with subsequent dehydration in a growing series of alcohols. Subsequently, the fragments were cleared with xylol for 2 hours and included in plastic polymers (Paraplast Plus, ST. Louis, Mo., USA). Subsequently, the materials were sectioned using a Slee CUT5062 RM 2165 microtome (Slee Mainz, Mainz, Germany) with 5 micrometer thickness, stained with hematoxylin-eosin and photographed using DM2500 photomicroscope (Leica, Munich, Germany). The diagnosis of urothelial lesions was classified according to the staging proposed by the common understanding of the World Health Organization/International Society of Urological Pathology (Epstein et al., 1998).

Cell Viability Assays

Cell viability of the MRB-CFI-1 nanodrug and its constituents was evaluated in grade II urinary bladder carcinoma cells (cell line 5637), with 24 hours of incubation. For this, two approaches (MTT and calcein/propidium iodide) were used, with different chemical agents to increase the robustness of the results and avoid artifacts. The 5637 cells were plated in a cell density of $2.0 \times 10^4$ and treated with serial dilutions of the compounds (12.5 mg, 6.25 mg, 3.13 mg, 1.56 mg and 0.39 mg) over 24 hours of incubation.

Statistical Analyses:

The histopathological analyses were evaluated using the ratio test. For these analyses, a 5% type I error was considered statistically significant.

Results:

In vivo toxicological and biochemical analyses of MRB-CFI-1: Serum levels of ALT, AST, alkaline phosphatase, urea and creatinine in rats, mice and rabbits treated intravesically with MRB-CFI-1 at doses of 20 mg/kg, 50 mg/kg and 100 mg/kg did not differ statistically from their respective controls (tables 5, 6 and 7), indicating that this compound did not present systemic toxic effects.

The urinary bladder, ureter and kidneys from rats, mice and rabbits in the control group did not present inflammation and histopathological alterations (FIGS. 10a, 10b, 10c, 11a, 11b, 12a and 12b; table 5). Rats from MRB-CFI-1 20 group showed minimal inflammation in the urinary bladder (100.0%), ureters (80.0%) and kidneys (60.0%) (FIGS. 10d, 10e, 10f; table 5). Moderate inflammation was observed in the urinary bladder (80.0%), ureters (80.0%) and kidneys (60.0%) of rats from MRB-CFI-1 50 group (FIGS. 10g, 10h, 10i, table 5). Rats from MRB-CFI-1 100 group showed intense inflammation in the urinary bladder (80.0%), ureters (80.0%) and kidneys (60.0%) (FIGS. 10j, 10k, 10l, table 5). Rats from MRB-CFI-1 50 and MRB-CFI-1 100 groups presented flat hyperplasia in the urinary bladder urothelium and ureters (FIGS. 10g, 10h, 10j and 10k).

Figure 11:
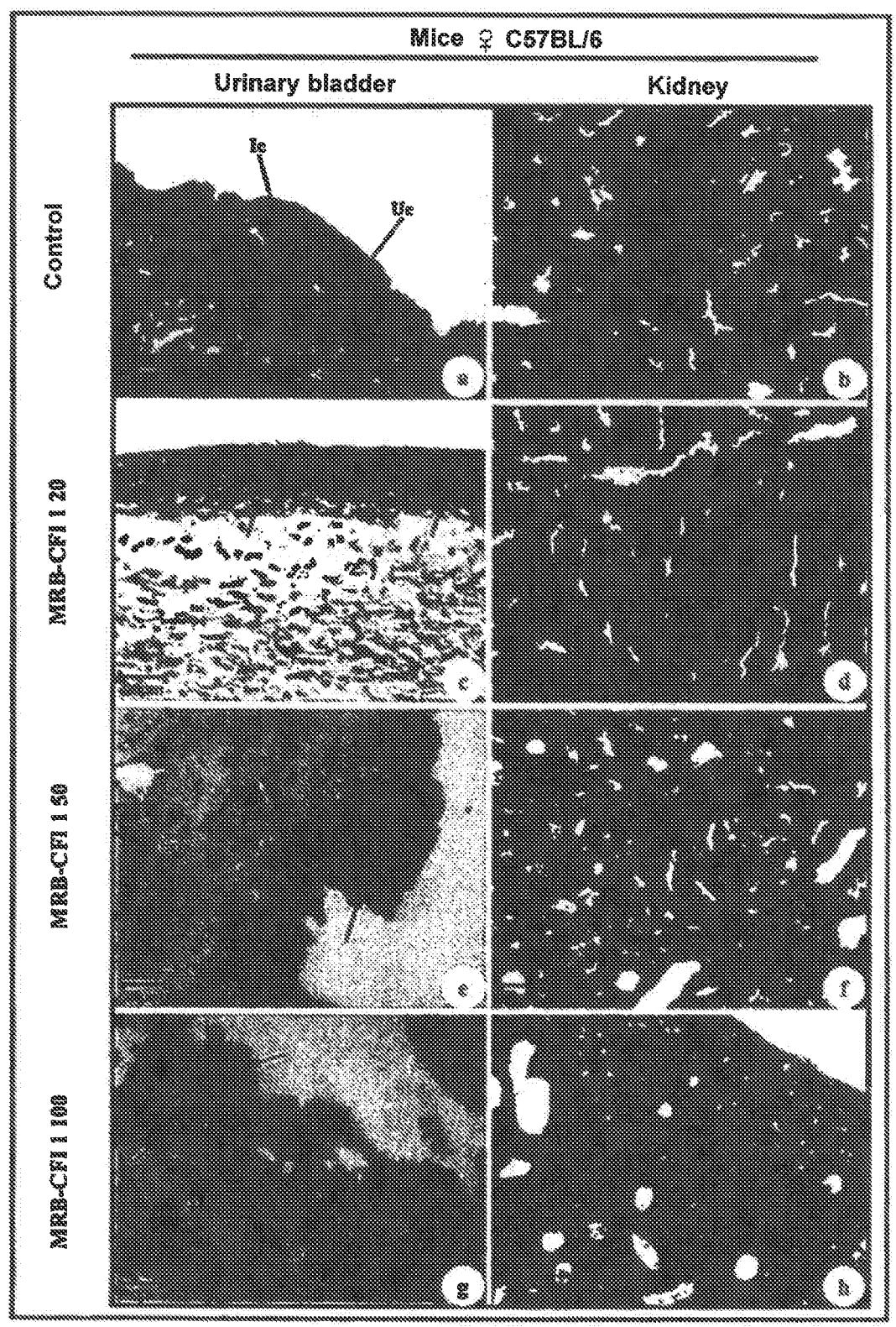
FIG. 11: Photomicrographies of the urinary bladder and mouse kidney of control groups (A, B), MRB-CFI-1 20 (c, d), MRB-CFI1 50 (e, f) and MRB-CFI1 100 (g, h). (a) normal urinary bladder urothelium consisting of 2-3 cell layers: one layer of basal cells (Bc), one layer of intermediate cells (Ic) and one superficial layer composed of umbrella cells (Uc). (b) and (d) Normal nephrons: glomeruli (Gl), podocytes (Pd), proximal contorted tubule (Pct), distal contorted tubule (DCT), macula densa (Md), urinary pole (Up) and vascular pole (Vp). (c) Minimal inflammation (asterisks and arrows) in the urinary bladder, (e) and (g) moderate inflammation (asterisks and arrows) and flat urothelial hyperplasia in the urinary bladder, (f) and (h) moderate inflammation (asterisks) in the nephrons. a-h: Gl—glomerulus, Lp—lamina propria, Ur—urothelium.
Figure 12:
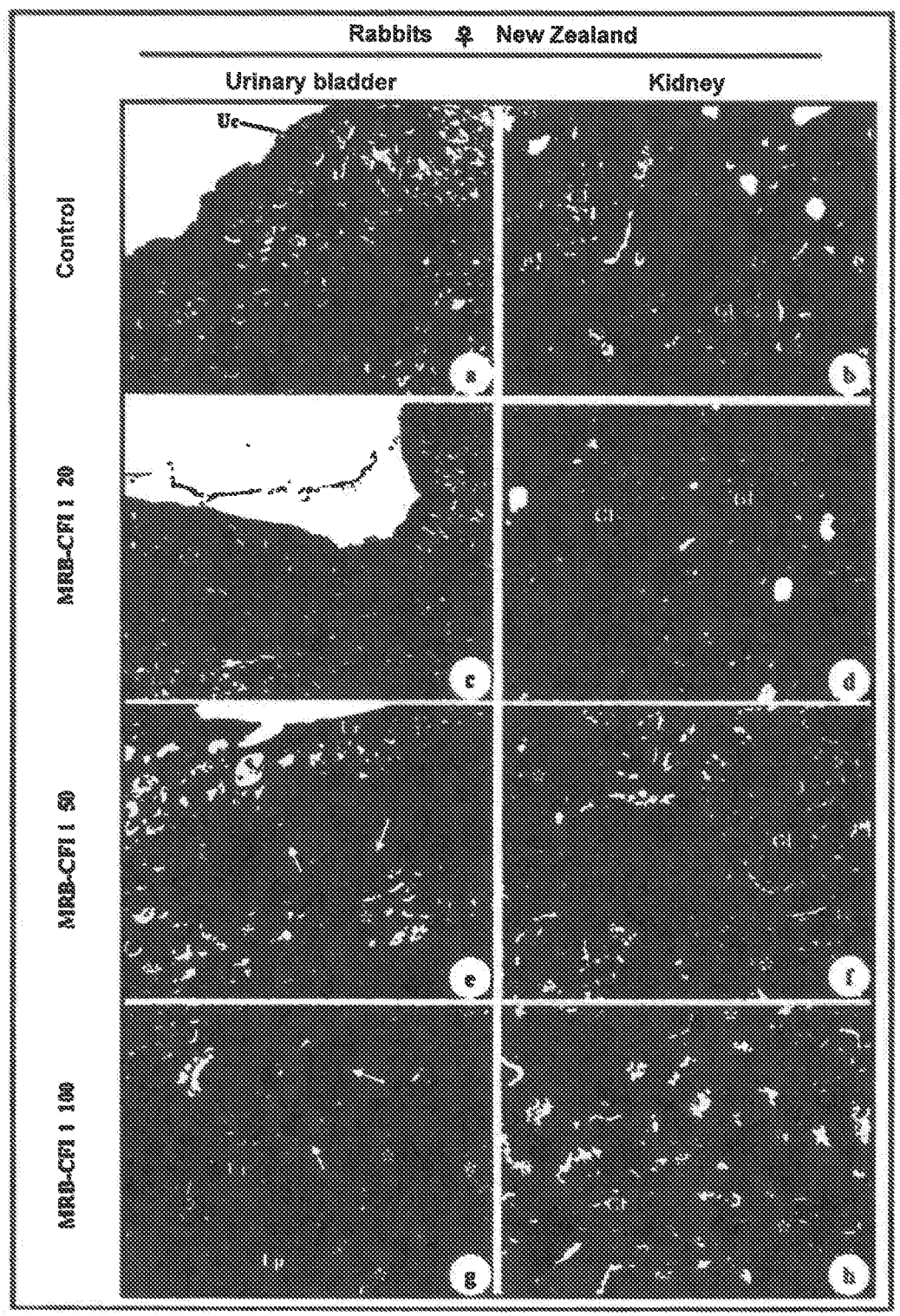
FIG. 12: Photomicrographies of the urinary bladder and rabbit kidney of control groups (a, b), MRB-CFI-1 20 (c, d), MRB-CFI1 50 (e, f) and MRB-CFI1 100 (g, h). (a) and (c) Normal urinary bladder urothelium consisting of 2-3 cell layers: one layer of basal cells (Bc), one layer of intermediate cells (Ic) and one superficial layer composed of umbrella cells (Uc). (b) and (d) Normal nephrons: glomeruli (Gl), podocytes (Pd), proximal contorted tubule (Pct), distal contorted tubule (DCT), macula densa (Md), urinary pole (Up) and vascular pole (Vp). (e) and (g) Moderate inflammation (asterisks and arrows) and flat urothelial hyperplasia in the urinary bladder, (f) and (h) moderate inflammation (asterisks) in the nephrons. a-h: Gl—glomerulus, Lp—lamina propria, Ur—urothelium.

Mice from MRB-CFI-1 20 group showed minimal inflammation in the urinary bladder (100.0%) and ureters (100.0%), and absence of inflammation in kidneys (FIGS. 11c, 11d, table 6). Moderate inflammation was observed in the urinary bladder (100.0%), ureters (00.0%) and kidneys (100.0%) of mice from the MRB-CFI-1 50 and MRB-CFI-1 100 groups (FIGS. 11e, 11f, 11g, 11h, table 6). Flat hyperplasia was observed in the urinary bladder urothelium and ureters from mice of the MRB-CFI-50 and MRB-CFI-1 100 groups (FIGS. 11e and 11g). Rabbits from MRB-CFI-1 50 and MRB-CFI-1 100 groups showed moderate inflammation in the urinary bladder (100.0%) and kidneys (00.0%), while the animals from MRB-CFI-1 20 group did not present inflammation nor histopathological alterations in the organs of the urinary system (FIGS. 12c, 12d, 12e, 12f, 12g, 12h, table 7). Flat hyperplasia was observed in the urinary bladder urothelium and ureters from rabbits of the MRB-CFI-50 and MRB-CFI-1 100 groups (FIGS. 12e and 12g).

Absence of inflammation and histopathological alterations were verified in the liver, spleen, stomach and pancreas of all animals from each species (tables 8, 9, 10).

TABLE 5

Toxicological and biochemical parameters for rats.

| Groups | ALT (U/L) | AST (U/L) | Alkaline phosphatase (U/L) | Urea (mg/dL) | Creatinine (mg/dL) |
|---|---|---|---|---|---|
| Control | 22.9 ± 3.2 a | 85.4 + 5.3 a | 176.7 ± 15.2 a | 38.5 ± 2.2 a | 0.55 ± 0.03 a |
| MRB-CFI-1 20 | 22.8 ± 4.1 a | 75.6 ± 9.1 a | 183.1 ± 13.4 a | 40.2 ± 4.0 a | 0.43 ± 0.04 a |
| MRB-CFI-1 50 | 26.5 ± 5.4 a | 73.3 ± 9.1 a | 178.6 ± 31.1 a | 40.0 ± 1.6 a | 0.49 ± 0.09 a |
| MRB-CFI-1 100 | 28.1 ± 10.4 a | 73.8 ± 10.6 a | 194.2 + 14.1 a | 40.8 ± 3.8 a | 0.51 ± 0.03 a |

Data expressed as mean±standard deviation (n=5 animals per group).
Two means followed by the same lowercase letter do not differ statistically, according to the Turkey test ($P<0.05$).

TABLE 6

Toxicological and biochemical parameters for mice.

| Groups | ALT (U/L) | AST (U/L) | Alkaline phosphatase (U/L) | Urea (mg/dL) | Creatinine (mg/dL) |
|---|---|---|---|---|---|
| Control | 11.7 ± 3.1 a | 92.4 ± 5.5 a | 154.1 ± 9.3 a | 36.0 + 7.1 a | 0.27 + 0.04 a |
| MRB-CFI-1 20 | 13.4 ± 2.7 a | 94.8 ± 5.5 a | 179.7 ± 7.8 a | 32.3 ± 4.9 a | 0.23 ± 0.05 a |
| MRB-CFI-1 50 | 14.1 + 2.7 a | 93.7 + 5.5 a | 185.3 ± 10.7 a | 25.9 ± 3.7 a | 0.34 + 0.14 a |
| MRB-CFI-1 100 | 13.7 ± 2.0 a | 94.4 ± 5.4 a | 187.5 ± 8.8 a | 26.6 ± 3.5 a | 0.31 + 0.08 a |

Data expressed as mean±standard deviation (n=5 animals per group).
Two means followed by the same lowercase letter do not differ statistically, according to the Turkey test ($P<0.05$).

TABLE 7

Toxicological and biochemical parameters for rabbits.

| Groups | ALT (U/L) | AST (U/L) | Alkaline phosphatase (U/L) | Urea (mg/dL) | Creatinine (mg/dL) |
|---|---|---|---|---|---|
| Control | 20.9 + 2.6 a | 42.0 ± 1.4 a | 129.0 ± 12.7 a | 39.7 ± 4.7 a | 0.90 ± 0.06 a |
| MRB-CFI-1 20 | 30.5 ± 2.1 a | 47.0 ± 1.4 a | 126.0 ± 9.9 a | 43.0 ± 4.2 a | 0.85 ± 0.15 a |
| MRB-CFI-1 50 | 33.4 ± 0.6 a | 41.0 ± 1.3 a | 137.5 ± 10.6 a | 40.2 ± 5.4 a | 0.94 ± 0.06 a |
| MRB-CFI-1 100 | 35.7 ± 1.8 a | 47.5 ± 2.1 a | 126.0 ± 19.8 a | 44.0 ± 4.2 a | 0.95 ± 0.08 a |

Data expressed as mean±standard deviation (n=b animals per group).
Two means followed by the same lowercase letter do not differ statistically, according to the Turkey test ($P<0.05$).

TABLE 8

Semiquantitative assessment of inflammation in the urinary bladder, ureters, kidneys, liver, spleen, pancreas and stomach for the 5 rats of each experimental group.

| | Groups | | | | | | | | | | | | | | | | | | | |
|---|---|---|---|---|---|---|---|---|---|---|---|---|---|---|---|---|---|---|---|---|
| | Control (n = 05) | | | | | MRB-CFI-1 20 (n = 05) | | | | | MRB-CFI-1 50 (n = 05) | | | | | MRB-CFI-1 100 (n = 05) | | | | |
| Organs | 1 | 2 | 3 | 4 | 5 | 1 | 2 | 3 | 4 | 5 | 1 | 2 | 3 | 4 | 5 | 1 | 2 | 3 | 4 | 5 |
| Bladder | 0 | 0 | 0 | 0 | 0 | 0 | 1 | 1 | 1 | 1 | 2 | 2 | 2 | 1 | 2 | 3 | 3 | 3 | 3 | 2 |
| Ureter | 0 | 0 | 0 | 0 | 0 | 0 | 1 | 1 | 1 | 1 | 2 | 2 | 2 | 1 | 2 | 3 | 3 | 3 | 3 | 2 |
| Kidney | 0 | 0 | 0 | 0 | 0 | 1 | 1 | 1 | 1 | 0 | 2 | 2 | 2 | 1 | 1 | 3 | 3 | 3 | 2 | 2 |
| Liver | 0 | 0 | 0 | 0 | 0 | 0 | 0 | 0 | 0 | 0 | 0 | 0 | 0 | 0 | 0 | 0 | 0 | 0 | 0 | 0 |
| Spleen | 0 | 0 | 0 | 0 | 0 | 0 | 0 | 0 | 0 | 0 | 0 | 0 | 0 | 0 | 0 | 0 | 0 | 0 | 0 | 0 |
| Pancreas | 0 | 0 | 0 | 0 | 0 | 0 | 0 | 0 | 0 | 0 | 0 | 0 | 0 | 0 | 0 | 0 | 0 | 0 | 0 | 0 |
| Stomach | 0 | 0 | 0 | 0 | 0 | 0 | 0 | 0 | 0 | 0 | 0 | 0 | 0 | 0 | 0 | 0 | 0 | 0 | 0 | 0 |

0, absence of inflammation, 1, minimal inflammation (less than five lymphocytes in an area of 0.25 mm$^2$), 2, moderate inflammation (mononuclear inflammatory cells scattered throughout the tissue, but still with visible stroma), 3, intense inflammation (mononuclear inflammatory cells densely infiltrating the tissues.

TABLE 9

Semiquantitative assessment of inflammation in the urinary bladder, ureters, kidneys, liver, spleen, pancreas and stomach for the 5 mice of each experimental group.

| | Groups | | | | | | | | | | | | | | | | | | | |
|---|---|---|---|---|---|---|---|---|---|---|---|---|---|---|---|---|---|---|---|---|
| | Control (n = 05) | | | | | MRB-CFI-1 20 (n = 05) | | | | | MRB-CFI-1 50 (n = 05) | | | | | MRB-CFI-1 100 (n = 05) | | | | |
| Organs | 1 | 2 | 3 | 4 | 5 | 1 | 2 | 3 | 4 | 5 | 1 | 2 | 3 | 4 | 5 | 1 | 2 | 3 | 4 | 5 |
| Bladder | 0 | 0 | 0 | 0 | 0 | 1 | 1 | 1 | 1 | 1 | 2 | 2 | 2 | 2 | 2 | 2 | 2 | 2 | 2 | 2 |
| Ureter | 0 | 0 | 0 | 0 | 0 | 1 | 1 | 1 | 1 | 1 | 2 | 2 | 2 | 2 | 2 | 2 | 2 | 2 | 2 | 2 |
| Kidney | 0 | 0 | 0 | 0 | 0 | 0 | 0 | 0 | 0 | 0 | 2 | 2 | 2 | 2 | 2 | 2 | 2 | 2 | 2 | 2 |
| Liver | 0 | 0 | 0 | 0 | 0 | 0 | 0 | 0 | 0 | 0 | 0 | 0 | 0 | 0 | 0 | 0 | 0 | 0 | 0 | 0 |
| Spleen | 0 | 0 | 0 | 0 | 0 | 0 | 0 | 0 | 0 | 0 | 0 | 0 | 0 | 0 | 0 | 0 | 0 | 0 | 0 | 0 |
| Pancreas | 0 | 0 | 0 | 0 | 0 | 0 | 0 | 0 | 0 | 0 | 0 | 0 | 0 | 0 | 0 | 0 | 0 | 0 | 0 | 0 |
| Stomach | 0 | 0 | 0 | 0 | 0 | 0 | 0 | 0 | 0 | 0 | 0 | 0 | 0 | 0 | 0 | 0 | 0 | 0 | 0 | 0 |

0, absence of inflammation, 1, minimal inflammation (less than five lymphocytes in an area of 0.25 mm$^2$), 2, moderate inflammation (mononuclear inflammatory cells scattered throughout the tissue, but still with visible stroma), 3, intense inflammation (mononuclear inflammatory cells densely infiltrating the tissues.

TABLE 10

Semiquantitative assessment of inflammation in the urinary bladder, ureters, kidneys, liver, spleen, pancreas and stomach for the 5 rabbits of each experimental group.

| | Groups | | | | | | | | | | | | | | | | | | | |
|---|---|---|---|---|---|---|---|---|---|---|---|---|---|---|---|---|---|---|---|---|
| | Control (n = 05) | | | | | MRB-CFI-1 20 (n = 05) | | | | | MRB-CFI-1 50 (n = 05) | | | | | MRB-CFI-1 100 (n = 05) | | | | |
| Organs | 1 | 2 | 3 | 4 | 5 | 1 | 2 | 3 | 4 | 5 | 1 | 2 | 3 | 4 | 5 | 1 | 2 | 3 | 4 | 5 |
| Bladder | 0 | 0 | 0 | 0 | 0 | 1 | 1 | 1 | 1 | 1 | 2 | 2 | 2 | 2 | 2 | 2 | 2 | 2 | 2 | 2 |
| Ureter | 0 | 0 | 0 | 0 | 0 | 1 | 1 | 1 | 1 | 1 | 2 | 2 | 2 | 2 | 2 | 2 | 2 | 2 | 2 | 2 |
| Kidney | 0 | 0 | 0 | 0 | 0 | 0 | 0 | 0 | 0 | 0 | 2 | 2 | 2 | 2 | 2 | 2 | 2 | 2 | 2 | 2 |
| Liver | 0 | 0 | 0 | 0 | 0 | 0 | 0 | 0 | 0 | 0 | 0 | 0 | 0 | 0 | 0 | 0 | 0 | 0 | 0 | 0 |
| Spleen | 0 | 0 | 0 | 0 | 0 | 0 | 0 | 0 | 0 | 0 | 0 | 0 | 0 | 0 | 0 | 0 | 0 | 0 | 0 | 0 |
| Pancreas | 0 | 0 | 0 | 0 | 0 | 0 | 0 | 0 | 0 | 0 | 0 | 0 | 0 | 0 | 0 | 0 | 0 | 0 | 0 | 0 |
| Stomach | 0 | 0 | 0 | 0 | 0 | 0 | 0 | 0 | 0 | 0 | 0 | 0 | 0 | 0 | 0 | 0 | 0 | 0 | 0 | 0 |

0, absence of inflammation, 1, minimal inflammation (less than five lymphocytes in an area of 0.25 mm$^2$), 2, moderate inflammation (mononuclear inflammatory cells scattered throughout the tissue, but still with visible stroma), 3, intense inflammation (mononuclear inflammatory cells densely infiltrating the tissues.

Figure 13:
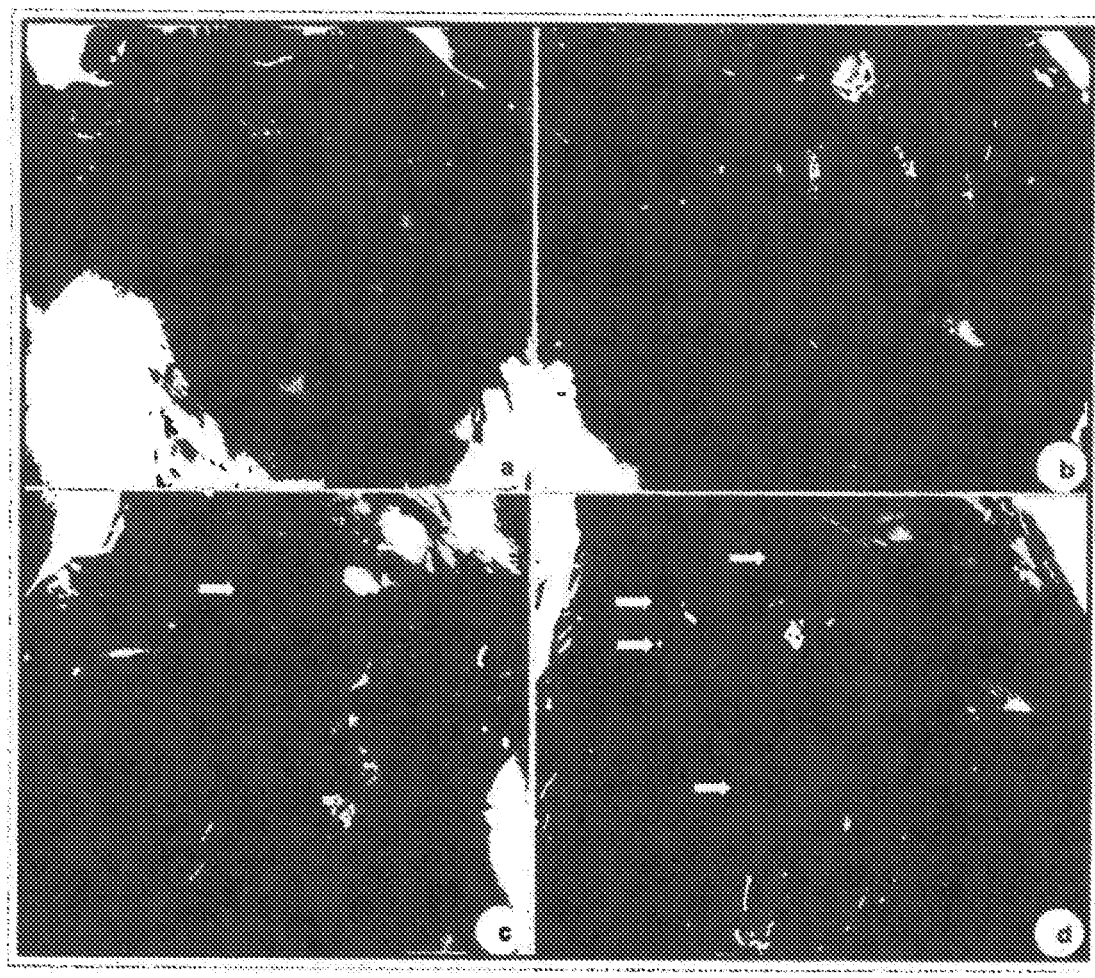
FIG. 13: Pictures of the abdominal cavity and macroscopic assessment of the peritoneum of rats from the control groups (a), CFI-1 (b) and MRB-CFI-1 (c, d), (a) normal abdominal cavity and peritoneum without signs of inflammation, (b) peritoneum with moderate signs of inflammation characterized by flushing, increased vascularization and hemorrhagic points (asterisks), as well as small clusters of phosphate crystals (arrows), (c), (d) intense peritoneal inflammation characterized by increased flushing, vascularization and haemorrhagic points (asterisks), and increased deposits of phosphate crystals (arrows) in the abdominal cavity.

Assessment of Peritoneal Inflammatory Response after Administration of CFI-1, P14-16 Protein and MRB-CFI-1 Compound:

The macroscopic analyses of the peritoneum disclosed that the animals from control groups (FIG. 13a) and P14-16 showed no inflammatory signs, as well as increased vascularization. All animals from group CFI-1 (FIG. 13b) presented moderate signs of peritoneal inflammation, which were characterized by flushing, increased vascularization and hemorrhagic points, and small clusters of phosphate crystals in the abdominal cavity. Regarding MRB-CFI-1 group, all animals presented intense peritoneal inflammation characterized by increased flushing, vascularization and hemorrhagic points (FIGS. 13c and 13d). In addition, there was an increase of deposits of phosphate crystals in the abdominal cavity. Thus, the present macroscopic results disclosed that compound MRB-CFI-1 was able to induce inflammatory response, which justifies its evaluation as an immunomodulator in the experiments in animals with non-muscle invasive bladder cancer (NMIBC) chemically induced, associated with its minimal or absent toxic effects.

Figure 14:
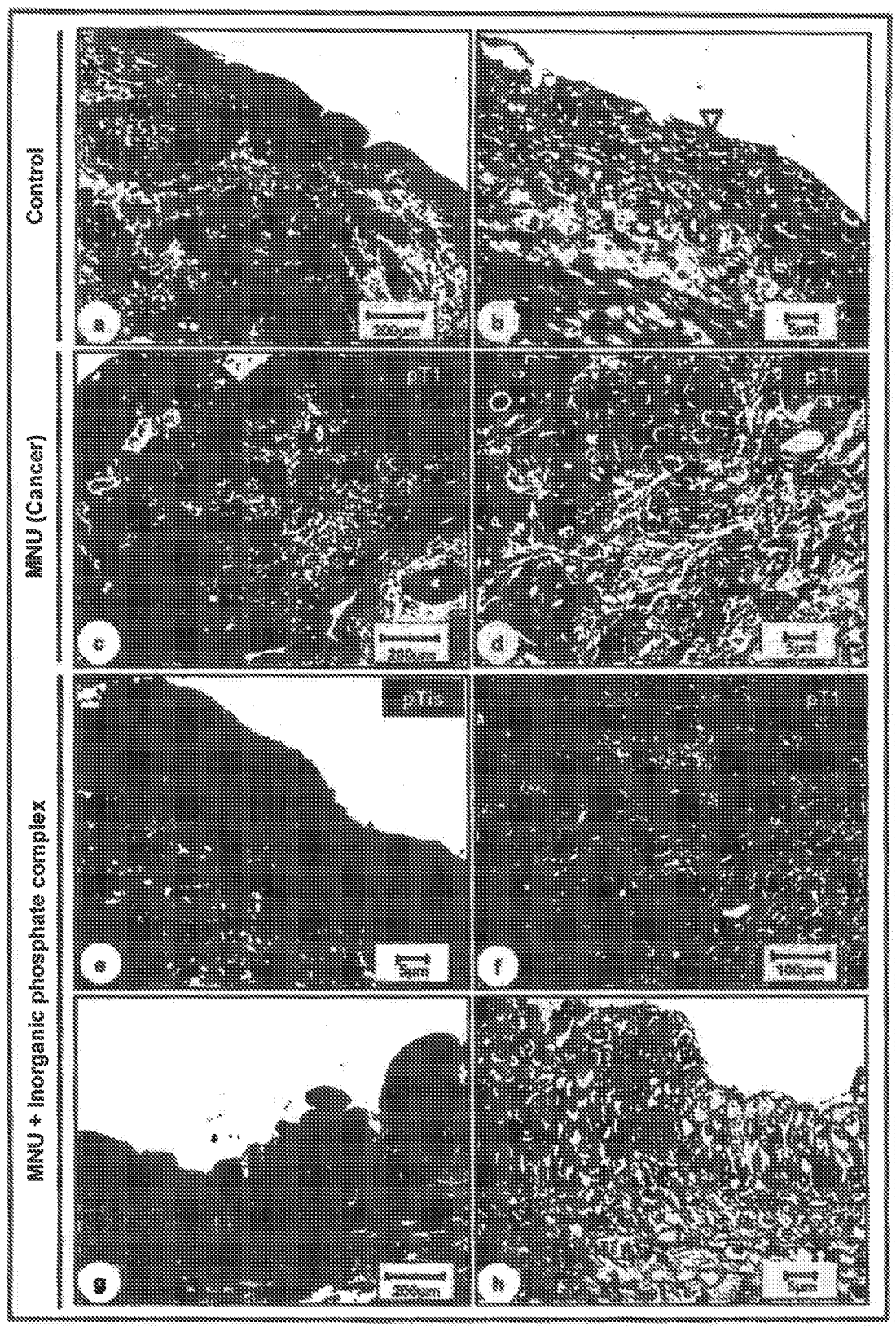
FIG. 14: Photomicrographs of the urinary bladders of control group (A, B), MNU (c, d) and MNU+inorganic phosphate complex 1 (CFI-1) (e, f, g, h). (a), (b) Normal urothelium consisting of 2-3 layers: a layer of basal cells (closed arrow head), an intermediate cell layer (arrow), and a superficial or apical layer composed of umbrella cells (open arrow head), (c), (d), (f) Invasive urothelial carcinoma (pT1): neoplastic cells arranged in small groups (asterisks)

Histopathological Analysis: Treatment of Non-Muscle Invasive Urinary Bladder Cancer (NMIBC) in Fischer 344 Rats:

The urinary tract of the control group did not present microscopic alterations (FIGS. 14a and 14b; table 11). The normal urothelium was composed of 2-3 layers: a layer of basal cells, an intermediate cell layer and a superficial or apical layer comprised by umbrella cells (FIGS. 14a and 14b).

In contrast, the urinary tract of the MNU Group (cancer) showed drastic histopathological alterations, such as: invasive urothelial carcinoma (pT1) (FIGS. 14c, 14d) and non-invasive urothelial carcinoma (pTa) in 60% and 40% of the animals, respectively (table 11). The pT1 carcinoma (FIGS. 14c, 14d, 14f) was characterized by neoplastic cells grouped in small groups or cords invading the connective mucosa, numerous mitotic figures and pleomorphic cells with enlarged nuclei and focal squamous differentiation.

The most frequent neoplastic lesions in the MNU group+ inorganic phosphate complex were the flat carcinoma in situ (pTis) (FIG. 14e) and the pT1 carcinoma (FIG. 14f), which occurred in 40% and 20% of the animals, respectively (table 11). The other animals did not present malignant lesions, and 20% of them presented flat hyperplasia (FIGS. 14g, 14h; table 11) and 20% normal bladder morphology, indicating that this treatment promoted 40% of tumor regression (table 11). pTis carcinoma (FIG. 14e) was characterized by a disorderly proliferation of urothelial cells in a flat urothelium, with accentuated cellular atypia characterized by bulky nuclei, reduction of cytoplasm and multiple and prominent nucleoli.

The histopathological analyses of the animals from MNU+P14-16 group had 40% of tumor regression, and 20% of them presented flat hyperplasia (FIGS. 15a, 15b; table 11) and 20% normal bladder morphology (table 11). The most frequent neoplastic lesions in this group were high-grade pTa carcinoma (FIGS. 15c, 15d) and pT1 carcinoma, both in 20% of the animals (table 11). Non-invasive pTa carcinoma was characterized by papillary or non-papillary lesions, urothelial cells with disorderly arrangement and with loss of polarity, hyperchromatic, pleomorphic nuclei and prominent nucleoli (FIGS. 15c, 15d).

The microscopic aspects of the urinary bladder of MRB-CFI-1 group were similar to those found in the control group. Normal urothelium was found in 40% of the animals (FIGS. 15e, 15f; table 11). The most frequent histopathological alteration in this group was flat hyperplasia (FIGS. 15g, 15h) that occurred in 40% of the animals (table 11), indicating that this compound promoted tumor regression in 80% of the animals. Flat hyperplasia was characterized by thickening of the urothelium and absence of cytological atypia (FIGS. 14h, 15a, 15b, 15g and 15h). pTis carcinoma occurred in 20% of the animals in this group (table 11).

TABLE 11

Percentage of histopathological alterations in the urinary bladder of rats from different experimental groups.

| Histopathology | Control (n = 20) | MNU (n = 20) | MNU + CFI-1 (n = 20) | MNU + P14-16 (n = 20) | MNU + MRB-CFI-1 (n = 20) |
|---|---|---|---|---|---|
| Normal | 20 (100%)* | — | 4 (20%) | 4 (20%) | 8 (40%) |
| Flat hyperplasia | — | — | 4 (20%) | 4 (20%) | 8 (40%)* |
| High-grade urothelial neoplasia-carcinoma in situ (pTis) | — | — | 8 (40%)* | — | 4 (20%) |
| Non-invasive urothelial carcinoma (pTa) | — | 8 (40%)* | — | 8 (40%) | — |
| Invasive urothelial carcinoma (pT1) | — | 12 (60%) | 4 (20%) | 4 (20%) | — |

*Statistical significance (ratio test, P < 0.0001). Benign lesions: flat hyperplasia; Malignant lesions: pTis, pTa and pT1.

Antigen Immunostaining: TLR4, TRIF, IRF3, INF-γ, TLR2, IKK-α, MyD88, IL-6 and TNF-α: Treatment of Non-Muscle Invasive Urinary Bladder Cancer (NMIBC) in Fischer 344 Rats:

Immunostainings for MyD88 and IKK-α were significantly moderated in the control, MNU+CFI-1, MNU+P14-16 and MRB-CFI-1 groups in relation to the MNU group, which presented weak immunoreactivity for these antigens (table 12). Also, the immunostaining for IL-6 and TNF-α were significantly moderate in the MNU group compared to the other experimental groups, indicating that the nanodrug MRB-CFI-1 and its constituents did not induce the pathway for producing inflammatory cytokines mediated by TLRs 2 and 4.

In contrast, the immunomarkers for TLR2, TLR4, TRIF, IRF3 and INF-γ were significantly intense in the urothelium of MRB-CFI-1 and control groups in comparison with the other experimental groups (table 12), indicating that the MRB-CFI-1 nanodrug was able to stimulate the interferon pathway mediated by TLRs 2 and 4. Also, the immunomarkers for these antigens were moderated in the MNU+CFI-1 and MNU+P14-16 groups in relation to the MNU Group (table 12).

TABLE 12

Mean immunostaining intensity for the different antigens in the urinary bladder of control, MNU, MNU + CFI-1, MNU + P14-16 and MNU + MRB-CFI-1 groups.

| Antigen groups | Control (n = 20) | MNU (n = 20) | MNU + CFI-1 (n = 20) | MNU + P14-16 (n = 20) | MNU + MRB-CFI-1 (n = 20) |
|---|---|---|---|---|---|
| TLR4 | 3 (91.8%)* | 1 (10.4%) | 2 (53.1%) | 2 (52.0%) | 3 (88.7%)* |
| TRIF | 3 (80.5%)* | 1 (8.6%) | 2 (50.2%) | 2 (57.2%) | 3 (90,4%)* |
| IRF-3 | 3 (87.5%)* | 1 (8.9%) | 2 (59.7%) | 2 (61.8%) | 3 (91.0%)* |
| IFN-γ | 3 (88.2%)* | 1 (9.5%) | 2 (60.2%) | 2 (64.9%) | 3 (91.0%)* |
| TLR2 | 3 (92.4%)* | 1 (15.0%) | 2 (51.0%) | 2 (56.3%) | 3 (89.7%)* |
| IKK-α | 2 (47.6%)* | 1 (20.3%) | 2 (50.1%)* | 2 (54.7%)* | 2 (50.4%)* |
| MyD88 | 2 (50.1%)* | 1 (17.4%) | 2 (47.3%)* | 2 (49.1%)* | 2 (48.8%)* |
| IL-6 | 1 (16.0%)* | 2 (47.2%)* | 1 (20.8%) | 1 (24.0%) | 1 (22.5%) |
| TNF-α | 1 (18.5%)* | 2 (49.0%)* | 1 (15.3%) | 1 (17.1%) | 1 (24.6%) |

0, absence of reactivity; 1, weak immunoreactivity (1 %-35% positive urothelial cells); 2, moderate immunoreactivity (36%-70% positive urothelial cells); 3, intense immunoreactivity (>70% positive urothelial cells).
*Statistical significance (ratio test, $P < 0.0001$).

Histopathological Analysis—Non-Muscle Invasive Urinary Bladder Cancer (NMIBC) Treatment in C57BL/6 Mice:

The urinary tract of the control group did not present microscopic alterations (table 13). In contrast, the urinary tract of the MNU Group (cancer) showed drastic histopathological alterations, such as: pT1 carcinoma, pTa carcinoma and pTis carcinoma in 20%, 20% and 60% of the animals, respectively (table 13).

The most frequent neoplastic lesions in the MNU+CFI-1 group were pTis carcinoma and pTa carcinoma, which occurred in 20% and 40% of the animals, respectively (table 13). The other animals did not present malignant lesions, with 20% of them presenting flat hyperplasia and 20% a pre-malignant lesion called low-grade intraurothelial neoplasia (table 13), indicating that this treatment promoted regression and inhibited tumor progression in 40% of the animals.

The histopathological analyses of the animals from group MNU+P14-16 presented 20% of tumor regression, and 20% of them presented flat hyperplasia (table 13). The most frequent neoplastic lesions in this group were pTis, pTa and pT1 carcinomas, both in 20%, 40% and 60% of the animals, respectively (table 13).

The microscopic aspects of the urinary bladder of MRB-CFI-1 group were similar to those found in the control group. Normal urothelium was found in 40% of the animals (table 13). Benign lesions such as flat hyperplasia, and pre-malignant lesions such as low-grade intraurothelial neoplasia, were found in 20% and 20% of the animals, respectively (table 13), indicating that this treatment promoted regression and inhibited tumor progression in 80% of the animals. The most frequent neoplastic lesion in this group was pTis carcinoma in 20% of the animals (table 13).

Clinical-Veterinary Assay: Treatment of Spontaneous Urinary Bladder Cancer in Dogs:

Several animal models experimentally induced for bladder cancer have been established, including chemically induced tumors. Although such animal models are in use in the research of bladder cancer, animal models in which the disease occurs naturally, mimic as close as possible to humans and may be useful to assess new therapies (Wu et al., 2006; Arantes-Rodrigues et al., 2013), including therapy with MRB-CFI-1.

Naturally occurring bladder cancer in dogs can provide an excellent model as it approaches human invasive bladder cancer, specifically high-grade invasive urothelial carcinoma in terms of cell and molecular characteristics; biologi-

TABLE 13

Percentage of histopathological alterations in the urinary bladder of mice from different experimental groups.

| Histopathology | Control (n = 20) | MNU (n = 20) | MNU + CFI-1 (n = 20) | MNU + P14-16 (n = 20) | MNU + MRB-CFI-1 (n = 20) |
|---|---|---|---|---|---|
| Normal | 20 (100%)* | — | — | — | 8 (40%) |
| Flat hyperplasia | — | — | 4 (20%)* | 4 (20%)* | 4 (20%)* |
| Low-grade intraurothelial neoplasia | — | — | 4 (20%)* | — | 4 (20%)* |
| High-grade intraurothelial neoplasia-carcinoma in situ (pTis) | — | 12 (60%)* | 4 (20%) | 4 (20%) | 4 (20%) |
| Non-invasive urotelial carcinoma (pTa) | — | 4 (20%) | 8 (40%)* | 8 (40%)* | — |
| Invasive urothelial carcinoma (pT1) | — | 4 (20%)* | — | 4 (20%)* | — |

*Statistical significance (ratio test, $P < 0.0001$). Benign lesions: flat hyperplasia; pre-malignant lesions: low-grade intraurothelial neoplasia; malignant lesions: pTis, pTa and pT1.

cal behavior, including sites and frequency of metastases; and response to therapy (Knapp et al., 2014).

To this end, the effects of intravesical immunotherapy with MRB-CFI-1 in the progression of bladder cancer are being evaluated in 20 dogs, attended at the veterinary clinic "Dr. Ronaldo Tizziani" (Campinas, Sao Paulo, Brazil). After the diagnosis of urothelial carcinoma and the consent of the dog's owners, the treatment with MRB-CFI-1 was initiated. The protocol for use of dogs in research was approved by the Ethics Committee on the Use of Animals (CEUA)—UNI-CAMP (protocol number: 4481-1/2017).

Dogs received 25 mg of MRB-CFI-1 dissolved in 2.0 mL of physiological saline solution 0.9% intravesically (probing) or by cystocentesis, depending on the conditions of access to the urinary bladder of each dog. These animals received a weekly dose of MRB-CFI-1 for six consecutive weeks. For maintenance therapy, the animals received a dose of MRB-CFI-1 every 15 days for 6 months and a monthly dose for another 6 months.

The therapeutic effects of MRB-CFI-1 were evaluated by ultrasound during the treatment cycle. Ultrasound evaluations were performed at the following times: before the first instillation, after the first instillation and after 3, 6, 18 and 24 instillations of MRB-CFI-1.

Six dogs completed the full therapeutic regimen with MRB-CFI-1, while 12 were in the maintenance phase and 2 in the induction phase. The following are the results of the 6 dogs, who completed the full therapeutic regimen: Dog 1: Dachshund breed, gender: female, age: 9 years; Dog 2: undefined breed (SRD), gender: female, age: 16 years; Dog 3: Dachshund breed, gender: female, age: 9 years; Dog 4: Teckel breed, Gender: female, age: 1 year; Dog 5: Lhasa Apso breed, gender: female, age: 13 years; Dog 5: Dachshund breed, gender: female, age: 12 years; Dog 6: Poodle breed, gender: female, age: 16 years.

Results:

Biochemical Analyses of Dogs with Urinary Bladder Cancer Undergoing Treatment with MRB-CFI-1:

Serum hemoglobin, leukocytes, platelets, hepatic function (ALT) and renal function (urea and creatinine) analyses indicated that the complete treatment with MRB-CFI-1 (24 applications) was not toxic to the 6 dogs, and many parameters such as hemoglobin, leukocytes and ALT reached normal values with the proposed treatment (table 14).

Therefore, these exams indicated that treatment with MRB-CFI-1 showed no signs of systemic toxicity at the proposed therapeutic dose.

Ultrasound Analyses of Dogs with Urinary Bladder Cancer Undergoing Treatment with MRB-CFI-1:

a) Dog 1: before the first instillation of MRB-CFI-1, it was observed the presence of tumor mass with irregular contours, mixed echogenicity and hyperechoic echotexture, measuring 3.08 cm×1.89 cm, and volume of 5.75 cm$^3$ (FIG. 16a, table 15). After 6 instillations of MRB-CFI-1, the tumor mass reduced 56.52% of its volume in relation to the initial ultrasound (FIGS. 16c, 16e, 16g, table 15). At the end of 24 instillations, the tumor mass reduced 79.30% of its volume (FIGS. 16i, 16k, table 15). At the beginning of treatment, dog 1 presented hematuria, which disappeared after the third application of MRB-CFI-1 and did not relapse even after the last application (table 15).

b) Dog 2: before the first instillation of MRB-CFI-1, it was observed the presence of tumor mass with irregular contours, mixed echogenicity and hyperechoic echotexture, measuring 3.42 cm×2.75 cm, and volume of 13.53 cm$^3$ (FIG. 16b, table 15). After 6 instillations of MRB-CFI-1, the tumor mass reduced 88.17% of its volume in relation to the initial ultrasound (FIGS. 16d, 16f, 16h, table 15). At the end of 24 instillations, the tumor mass reduced 93.93% of its volume (FIG. 16j, 16l, table 15). At the beginning of treatment, dog 2 presented hematuria, which disappeared after the third application of MRB-CFI-1 and did not relapse even after the last application (table 15).

c) Dog 3: before the first instillation of MRB-CFI-1, it was observed the presence of tumor mass with irregular contours, mixed echogenicity and hyperechoic echotexture, measuring 4.22 cm×2.60 cm, and volume of 14.93 cm$^3$ (FIG. 17a, table 15). After 6 instillations of MRB-CFI-1, the tumor mass reduced 61.35% of its volume in relation to the initial ultrasound (FIGS. 17c, 17e, 17g, table 15). At the end of 24 instillations, the tumor mass reduced 81.0% of its volume (FIGS. 17i, 17k, table 15). At the beginning of treatment, Dog 3 presented hematuria, which disappeared after the eighteenth application of MRB-CFI-1 (Table 15), without relapse after the end of treatment.

d) Dog 4: before the first instillation of MRB-CFI-1, it was observed the presence of tumor mass with irregular contours, mixed echogenicity and hyperechoic echotexture, measuring 3.91 cm×1.84 cm, and volume of 6.92 cm$^3$ (FIG. 17b, table 15). After 6 instillations of MRB-CFI-1, the tumor mass reduced 48.84% of its volume in relation to the initial ultrasound (FIGS. 17d, 17f, 17h, table 15). At the end of 24 instillations, the tumor mass reduced 82.22% of its volume (FIG. 17j, 17l, table 15). At the beginning of treatment, Dog 4 presented hematuria, which disappeared after the eighteenth application of MRB-CFI-1 (Table 15), without relapse after the end of treatment.

e) Dog 5: before the first instillation of MRB-CFI-1, it was observed the presence of tumor mass with irregular contours, mixed echogenicity and hyperechoic echotexture, measuring 2.25 cm×1.86 cm, and volume of 4.07 cm$^3$ (FIG. 18a, table 15). After 6 instillations of MRB-CFI-1, the tumor mass reduced 44.71% of its volume in relation to the initial ultrasound (FIGS. 18c, 18e, 18g, table 15). At the end of 24 instillations, the tumor mass reduced 84.5% of its volume (FIGS. 18i, 18k, table 15). At the beginning of treatment, dog 5 presented hematuria, which disappeared only after the last application (table 15).

f) Dog 6: before the first instillation of MRB-CFI-1, it was observed the presence of tumor mass with irregular contours, mixed echogenicity and hyperechoic echotexture, measuring 2.84 cm×2.73 cm, and volume of 11.08 cm$^3$ (FIG. 18b, table 15). After 6 instillations of MRB-CFI-1, the tumor mass reduced 74.45% of its volume in relation to the initial ultrasound (FIGS. 18d, 18f, 18h, table 15). At the end of 24 instillations, the tumor mass reduced 86.28% of its volume (FIG. 18j, 18l, table 15). Dog 6 did not present hematuria since the beginning of treatment until the end (table 15).

Thus, these results indicated that intravesical immunotherapy with MRB-CFI-1 was effective in reducing and preventing the progression of urothelial neoplastic lesions in spontaneous cancer of the canine urinary bladder.

Cell Viability Assays

Cell viability of MRB-CFI-1 and its components, CFI-1 and protein P14-16, was 76.01%±12.39, 68.63%±9.47 and 75.71%±11.52, respectively, using the maximum concentration of 12.5 mg, as denoted in the MTT reduction assay (FIG. 19A).

FIG. 19B demonstrates the impact of treatment with MRB-CFI-1 on cell membrane integrity. In addition, negative cells for calcein were observed, indicating loss of cell viability, as well as positive cells for propidium iodide (PI), indicating cell death. The results with 12.5 mg of MRB-CFI-1 compound showed 75.25%±6.19 of positive calcein and 25.50%±2.52 of positive PI for cell death. Therefore, all techniques reported comparable dose-response ratio, and the nanocompound MRB-CFI-1 showed low toxicity, as expected from drugs with immunomodulatory properties.

TABLE 14

Clinical evaluation of dogs before and after intravesical treatments with MRB-CFI-1.
Biochemical parameters

| Therapeutical scheme | Hemoglobin (g/dl) | Leukocytes (mm³) | Platelets (mm³) | ALT (U/L) | Urea (mg/dl) | Creatinine (mg/dL) |
|---|---|---|---|---|---|---|
| Before 1st instillation | 10.6 | 29,900 | 355,000 | 95.0 | 36.0 | 1.20 |
| Dog 1 after 1st instillation | 11.8 | 16,300 | 400,000 | 88.0 | 51.0 | 0.85 |
| After 24th instillation | 12.1 | 13,000 | 375,000 | 81.0 | 42.0 | 0.98 |
| Before 1st instillation | 12.6 | 28,000 | 455,000 | 188.0 | 25.0 | 1.10 |
| Dog 2 after 6th instillation | 12.0 | 16,300 | 350,000 | 129.0 | 35.0 | 0.80 |
| After 24th instillation | 13.1 | 11,000 | 400,000 | 68.0 | 22.0 | 1.00 |
| Before 1st instillation | 12.0 | 7,900 | 1,100,000 | 46.0 | 39.0 | 1.16 |
| Dog 3 after 6th, instillation | 13.9 | 8,600 | 759,000 | 58.0 | 45.0 | 0.94 |
| After 24th instillation | 14.7 | 12,900 | 300,000 | 41.0 | 50.0 | 0.90 |
| Before 1st instillation | 11.4 | 15,800 | 430,000 | 64.0 | 54.0 | 1.15 |
| Dog 4 after 6th, instillation | 12.3 | 18,800 | 390,000 | 80.0 | 53.0 | 0.78 |
| After 24th instillation | 12.0 | 17,000 | 410,000 | 84.0 | 56.0 | 0.66 |
| Before 1st instillation | 12.7 | 10,500 | 260,000 | 33.0 | 31.0 | 0.62 |
| Dog 5 after 6th, instillation | 12.1 | 9,600 | 334,000 | 50.0 | 40.0 | 1.15 |
| After 24th instillation | 12.5 | 11,200 | 420,000 | 45.0 | 52.0 | 0.77 |
| Before 1st instillation | 14.2 | 9,100 | 260,000 | 52.0 | 34.0 | 0.85 |
| Dog 6 after 6st instillation | 13.9 | 8,300 | 360,000 | 40.0 | 31.0 | 0.88 |
| After 24th instillation | 14.7 | 7,900 | 330,000 | 48.0 | 33.0 | 0.92 |

Reference values: Hemoglobin: After 1 year (12-18 g/dl); Leukocytes: After 1 year (6,000-18,000/mm³); Platelets: 150,000-500,000/mm³; ALT: 10-88 U/I; Urea: 15-65 mg/dl; Creatinine: 0.5-1.5 mg/dl.

TABLE 15

Ultrasound assessments of tumor size, volume and reduction compared to the presence of red blood cells in dogs urine before and after intravesical treatments with MRB-CFI-1.

| | Therapeautic regimen | Length (cm) | Width (cm) | Volume (cm³) | Tumor reduction (%) | Red blood cells (p/ml) |
|---|---|---|---|---|---|---|
| Dog 1 | Before 1st instillation | 3.08 | 1.89 | 5.75 | — | 50,000 |
| | After 1st instillation | 2.19 | 2.09 | 5.00 | 13.04 | 30,000 |
| | After 3rd instillation | 2.06 | 1.82 | 3.57 | 37.91 | 6,000 |
| | After 6th instillation | 1.60 | 1.87 | 2.50 | 56.52 | 4,000 |
| | After 18th instillation | 1.66 | 1.44 | 1.80 | 68.69 | 1,000 |
| | After 24th instillation | 1.61 | 1.19 | 1.19 | 79.30 | 200 |
| Dog 2 | Before 1st instillation | 3.42 | 2.75 | 13.53 | — | 70,000 |
| | After 1st instillation | 3.08 | 1.99 | 6.38 | 52.84 | 10,000 |
| | After 3rd instillation | 2.66 | 1.81 | 4.56 | 66.29 | 3,000 |
| | After 6th instillation | 1.54 | 1.41 | 1.60 | 88.17 | 500 |
| | After 18th instillation | 1.79 | 1.12 | 1.17 | 91.35 | 200 |
| | After 24th instillation | 1.94 | 0.90 | 0.82 | 93.93 | 300 |
| Dog 3 | Before 1st instillation | 4.22 | 2.60 | 14.93 | — | 120.000 |
| | After 1st instillation | 3.68 | 2.11 | 8.57 | 42.59 | 90,000 |
| | After 3rd instillation | 3.22 | 2.33 | 9.15 | 38.71 | 75,000 |
| | After 6th instillation | 3.19 | 1.86 | 5.77 | 61.35 | 15,000 |
| | After 18th instillation | 2.63 | 1.66 | 3.79 | 74.61 | 3,000 |
| | After 24th instillation | 2.58 | 1.45 | 2.83 | 81.00 | 900 |

TABLE 15-continued

Ultrasound assessments of tumor size, volume and reduction compared to the presence of red blood cells in dogs urine before and after intravesical treatments with MRB-CFI-1.

|  | Therapeautic regimen | Ultrasound parameters of the tumor | | | | Urine parameter I |
|---|---|---|---|---|---|---|
|  |  | Length (cm) | Width (cm) | Volume (cm$^3$) | Tumor reduction (%) | Red blood cells (p/ml) |
| Dog 4 | Before 1$^{st}$ instillation | 3.91 | 1.84 | 6.92 | — | 960,000 |
|  | After 1$^{st}$ instillation | 3.48 | 1.92 | 6.71 | 3.03 | 150,000 |
|  | After 3$^{rd}$ instillation | 4.14 | 1.74 | 6.56 | 5.20 | 78,000 |
|  | After 6$^{th}$ instillation | 2.76 | 1.53 | 3.38 | 48.84 | 24,000 |
|  | After 18$^{th}$ instillation | 1.96 | 1.31 | 1.76 | 74.56 | 6,000 |
|  | After 24$^{th}$ instillation | 2.35 | 1.00 | 1.23 | 82.22 | 2,000 |
| Dog 5 | Before 1$^{st}$ instillation | 2.25 | 1.86 | 4.07 | — | 464,000 |
|  | After 1$^{st}$ instillation | 2.19 | 1.81 | 3.75 | 7.86 | 200,000 |
|  | After 3$^{rd}$ instillation | 1.96 | 1.85 | 3.51 | 13.75 | 98,000 |
|  | After 6$^{th}$ instillation | 1.94 | 1.49 | 2.25 | 44.71 | 50,000 |
|  | After 18$^{th}$ instillation | 1.61 | 1.55 | 2.02 | 50.36 | 12,000 |
|  | After 24$^{th}$ instillation | 1.27 | 0.98 | 0.63 | 84.50 | 3,000 |
| Dog 6 | Before 1$^{st}$ instillation | 2.84 | 2.73 | 11.08 | — | 1,500 |
|  | After 1$^{st}$ instillation | 2.57 | 2.64 | 9.12 | 17.68 | 1,000 |
|  | After 3$^{rd}$ instillation | 3.03 | 2.06 | 6.70 | 39.53 | 2,500 |
|  | After 6$^{th}$ instillation | 2.34 | 1.52 | 2.83 | 74.45 | 1,500 |
|  | After 18$^{th}$ instillation | 2.49 | 1.20 | 2.02 | 81.76 | 1,000 |
|  | After 24$^{th}$ instillation | 2.69 | 1.04 | 1.52 | 86.28 | 1,200 |

Erythrocytes reference value (urine I): up to 6,000 p/ml

Analysis of therapeutic adjuvancy of intravesical immunotherapy with MRB-CFI-1 and systemic chemotherapy with cisplatin in non-muscle invasive bladder cancer (CBNMI)

The histopathological effects of intravesical immunotherapy with MRB-CFI-1 combined with systemic chemotherapy with systemic cisplatin were verified in Fischer 344 female rats, chemically induced to non-muscle invasive bladder cancer (CBNMI), as per the method already described above. After inducing NMIBC with N-methyl-N-nitrosourea (MNU), the animals were distributed in four experimental groups (n=7 animals per group): group 1 (cancer): received an intravesical dose of 0.2 mL of physiological solution 0.9% for 6 consecutive weeks; group 2 (cancer+MRB-CFI-1): received an intravesical dose of 20 mg/kg of compound MRB-CFI-1 for 6 consecutive weeks; group 3 (cancer+cisplatin): received an intraperitoneal dose of 0.25 mg/kg cisplatin once a week for 4 consecutive weeks; group 4 (cancer+MRB-CFI-1+cisplatin): received simultaneous treatment with MRB-CFI-1 and cisplatin in the same concentrations and through the same administration pathways as groups 2 and 3. The protocol for use of animals in research was approved by the Ethics Committee on the Use of Animals (CEUA)—UNICAMP (protocol number: 4324-1).

The results showed urothelial carcinoma with invasion of lamina propria (pT1) and papillary carcinoma (pTa) in 100% of animals in the cancer group.

The animals treated systemically with cisplatin showed a decrease in the progression of urothelial neoplastic lesions in 14.28% of the animals, which presented a benign lesion characterized by papillary hyperplasia (table 16). The most frequent neoplastic lesions in this group were carcinoma in situ (pTis), pTa carcinoma and pT1 carcinoma in 14.28%, 57.14% and 14.28% of the animals, respectively (table 16).

The animals treated with intravesical MRB-CFI-1 showed a 42.85% decrease in the progression of urothelial neoplastic lesions, which presented normal urothelium (table 16). The most frequent neoplastic lesions in this group were pTis carcinoma and pTa carcinoma in 28.57% and 28.57% of the animals, respectively (table 16).

The treatment combined with intravesical immunotherapy with MRB-CFI-1 and systemic chemotherapy with cisplatin showed better histopathological recovery of the cancer state and decreased progression of urothelial neoplastic lesions in 71.42% of the animals, of which 42.85% had normal urothelium and 28.57% had a benign lesion characterized by flat hyperplasia (table 16). The most frequent neoplastic lesion in this group was pTis carcinoma in 28.57% of the animals (table 16).

Thus, it can be concluded that the combination of intravesical immunotherapy with MRB-CFI-1 and systemic cisplatin may be considered a valuable option for the treatment of patients who do not respond to standard treatment with BCG and/or who do not meet the criteria for early cystectomy.

TABLE 16

Percentage of histopathological alterations in the urinary bladder of rats from different experimental groups.

| Urothelial lesions | | Group 1 (n = 7) | Group 2 (n = 7) | Group 3 (n = 7) | Group 4 (n = 7) |
|---|---|---|---|---|---|
| No lesion | Normal urothelium | — | 42.85% (3)* | — | 42.85% (3)* |
| Benign lesions | Flat hyperplasia | — | — | — | 28.57% (2)* |
|  | Papilliferous hyperplasia | — | — | 14.28% (1) | — |
| Malignant lesions | Carcinoma in situ (Ptis) | — | 28.57% (2)* | 14.28% (1) | — |
|  | Papillary carcinoma (pTa) | 42.85% (3)* | 28.57% (2) | 57.14% (4)* | 28.57% (2) |
|  | Urothelial carcinoma with lamina propria invasion (pT1) | 57.14% (4)* | — | 14.28% (1) | — |

Group 1: cancer, group 2: cancer + MRB-CFI-1, group 3: cancer + cisplatin, group 4: cancer + cisplatin + MRB-CFI-1.
*Statistical significance (ratio test, P < 0.0001).

Results—Exemplary Embodiments (I) and (II)

The characterization of CFI-1 with pH control in the absence (PI BR 10 2017 012768 0) (CFI-1-PI BR-2017) and the presence of monoethanolamine are as follows:

Elementary Analysis:

(A) CFI-1 (obtained as defined in the exemplary embodiment (I)): C (0.05%), H (7.02%), N (5.35%). (B) CFI-1 (obtained as defined in the exemplary embodiment (II)): C (0.08%), H (6.92%), N (5.33%).

Analysis of XPS or X-Ray-Excited Photoelectron Spectroscopy:

(A) CFI-1 (obtained as defined in the exemplary embodiment (I)): P (16.4%), Mg (19.1%), N (4.2%), O (60.3%), P/Mg ratio=0.9. (B) CFI-1 (obtained as defined in the exemplary embodiment (II)): P (16.9%), Mg (16.7%), N (5.0%) and O (61.3%), P/Mg ratio=1.0.

Size (Nm) and Surface Charge (Zeta Potential, mV):

(A) CFI-1 (obtained as defined in the exemplary embodiment (I)): shows a nanoparticle size value of 310.3, ±56.9 nm; and zeta potential of −21.8±5.8 mV. (B) CFI-1 (obtained as defined in the exemplary embodiment (II)): shows a nanoparticle size value of 449.6±116.6 nm; and zeta potential of −20.0±5.1 mV.

X-Ray Fluorescence Spectroscopic Analysis (XRF):

(A) CFI-1 (obtained as defined in the exemplary embodiment (I)): $PO_4$ (55.06%), Mg (16.88%), $NH_4$ (27.68), $PO_4$/Mg ratio=3.36. (B) CFI-1 (obtained as defined in the exemplary embodiment (II)): $PO_4$ (56.43%), Mg (17.61%), $NH_4$ (25.13), $PO_4$/Mg ratio=3.02.

X-Ray Diffraction Pattern (XRD)

FIG. 20 clearly shows that the CFI-1-PIBR-2017 (A), obtained as defined in the exemplary embodiment (I), presents the same characteristics of crystalline diffraction as the CFI-1+ethanolamine (B), obtained as defined in the exemplary embodiment (II). FIG. 20C shows the superposition of the two XRD figures.

The invention claimed is:

1. A method for treating cancer in a subject, the method comprising administering to the subject a compound selected from the group consisting of $NH_4MgPO_4 \times 6H_2O$, $(NH_4)2MgH_2(PO_4)_2 \times 4H_2O$, $(NH_4)2Mg_3(HPO_4)_4 \times 8H_2O$ and $NH_4MgPO_4 \times H_2O$ associated or not to hydrolytic enzymes, which are known to have immunomodulatory activities.

2. The method according to claim 1, wherein the cancer is prostate, bladder, colorectal, mastocytoma or lymphoma cancer.

3. The method according to claim 1, wherein the compound is administered in a pharmaceutically acceptable carrier.

* * * * *